(12) United States Patent
Davidson et al.

(10) Patent No.: US 12,403,081 B2
(45) Date of Patent: Sep. 2, 2025

(54) METHOD OF ASSESSING AND TREATING CELLULITE

(71) Applicant: Endo Operations Limited, Dublin (IE)

(72) Inventors: Jeffrey Davidson, Downingtown, PA (US); Michael McLane, Lansdale, PA (US); Genzhou Liu, North Wales, PA (US)

(73) Assignee: Endo Operations Limited, Ballsbridge (IE)

( * ) Notice: Subject to any disclaimer, the term of this patent is extended or adjusted under 35 U.S.C. 154(b) by 0 days.

(21) Appl. No.: 18/482,998

(22) Filed: Oct. 9, 2023

(65) Prior Publication Data
US 2024/0041744 A1 Feb. 8, 2024

Related U.S. Application Data

(62) Division of application No. 17/461,481, filed on Aug. 30, 2021, now Pat. No. 11,813,347, which is a
(Continued)

(51) Int. Cl.
*A61K 8/66* (2006.01)
*A61B 5/00* (2006.01)
(Continued)

(52) U.S. Cl.
CPC ................ *A61K 8/66* (2013.01); *A61B 5/103* (2013.01); *A61B 5/44* (2013.01); *A61B 5/441* (2013.01);
(Continued)

(58) Field of Classification Search
CPC ...... A61K 8/66; A61K 38/4886; A61B 5/103; A61B 5/44; A61B 5/441; A61B 5/444;
(Continued)

(56) References Cited

U.S. PATENT DOCUMENTS 3,821,364 A 6/1974 Chiulli et al.
4,338,000 A 7/1982 Kamimori et al.
(Continued)

FOREIGN PATENT DOCUMENTS

AU 2006206393 A1 7/2006
BR PI0607280-1 A2 8/2009
(Continued)

OTHER PUBLICATIONS

M. De La Casa , "Intra- and inter-observer reliability of the application of the cellulite severity scale to a Spanish female population: CSS reliability in a Spanish female population", Journal of the European Academy of Dermatology Andvenereology, pub. Apr. 6, 2012. (Year: 2012).*

(Continued)

*Primary Examiner* — Mekonen T Bekele
(74) *Attorney, Agent, or Firm* — BakerHostetler

(57) ABSTRACT

The present disclosure relates to a method for rating the severity of cellulite on a thigh or buttock in a human subject by utilizing a photonumeric scale that provides reliable results from physician-to-physician and patient-to-patient.

19 Claims, 14 Drawing Sheets
(14 of 14 Drawing Sheet(s) Filed in Color)

0 None
No dimples or evident cellulite

1 Almost None
Few dimples that are mostly superficial in depth

Related U.S. Application Data division of application No. 15/909,991, filed on Mar. 1, 2018, now Pat. No. 11,123,280.

(60) Provisional application No. 62/607,188, filed on Dec. 18, 2017, provisional application No. 62/485,705, filed on Apr. 14, 2017, provisional application No. 62/465,622, filed on Mar. 1, 2017.

(51) Int. Cl.
| | |
|---|---|
| *A61B 5/103* | (2006.01) |
| *A61K 38/48* | (2006.01) |
| *A61Q 19/06* | (2006.01) |
| *A61B 5/107* | (2006.01) |

(52) U.S. Cl.
CPC ............ *A61B 5/444* (2013.01); *A61B 5/4848* (2013.01); *A61K 38/4886* (2013.01); *A61Q 19/06* (2013.01); *C12Y 304/24003* (2013.01); *A61B 5/1079* (2013.01)

(58) Field of Classification Search
CPC .... A61B 5/4848; A61B 5/1079; A61Q 19/06; C12Y 304/24003; A61P 43/00
See application file for complete search history.

(56) References Cited

U.S. PATENT DOCUMENTS

| | | | |
|---|---|---|---|
| 4,338,300 | A | 7/1982 | Gelbard |
| 4,524,065 | A | 6/1985 | Pinnell |
| 4,645,668 | A | 2/1987 | Pinnell |
| 4,732,758 | A | 3/1988 | Hurion et al. |
| 5,252,461 | A | 10/1993 | Weisbart |
| 5,252,481 | A | 10/1993 | Holjevac et al. |
| 5,256,140 | A | 10/1993 | Fallick |
| 5,332,503 | A | 7/1994 | Lee et al. |
| 5,393,792 | A | 2/1995 | Stern et al. |
| 5,422,103 | A | 6/1995 | Stern et al. |
| 5,462,739 | A | 10/1995 | Dan et al. |
| 5,514,340 | A | 5/1996 | Lansdorp et al. |
| 5,514,370 | A | 5/1996 | Stern et al. |
| 5,589,171 | A | 12/1996 | Wegman |
| 5,705,170 | A | 1/1998 | Kong et al. |
| 5,753,485 | A | 5/1998 | Dwulet et al. |
| 5,753,785 | A | 5/1998 | Reddy et al. |
| 5,830,741 | A | 11/1998 | Dwulet et al. |
| 5,952,215 | A | 9/1999 | Dwulet et al. |
| 5,989,888 | A | 11/1999 | Dwulet et al. |
| 6,022,539 | A | 2/2000 | Wegman |
| 6,086,872 | A | 7/2000 | Wegman |
| 6,086,877 | A | 7/2000 | Nishioka et al. |
| 6,086,887 | A | 7/2000 | Parrott |
| 6,146,626 | A | 11/2000 | Markert et al. |
| 6,280,993 | B1 | 8/2001 | Yamato et al. |
| 6,335,388 | B1 | 1/2002 | Fotinos |
| 6,358,539 | B1 | 3/2002 | Murad |
| 6,475,764 | B1 | 11/2002 | Burtscher et al. |
| 6,953,583 | B1 | 10/2005 | Ghisalberti |
| 6,958,150 | B2 | 10/2005 | Wegman et al. |
| 7,083,964 | B2 | 8/2006 | Kurfuerst et al. |
| RE39,941 | E | 12/2007 | Wegman |
| 7,355,027 | B2 | 4/2008 | Brehm et al. |
| 7,622,130 | B2 | 11/2009 | Kolodney et al. |
| 7,811,560 | B2 | 10/2010 | Sabatino et al. |
| 7,824,673 | B2 | 11/2010 | Wegman et al. |
| 7,854,929 | B2 | 12/2010 | Badalemente et al. |
| 8,323,643 | B2 | 12/2012 | Badalemente et al. |
| 8,380,531 | B2 | 2/2013 | Paty et al. |
| 9,744,138 | B2 | 8/2017 | Leppert et al. |
| 9,757,435 | B2 | 9/2017 | Herber |
| 10,123,959 | B2 * | 11/2018 | Badalamente .......... A61P 17/00 |
| 2002/0036328 | A1 | 3/2002 | Richards et al. |
| 2003/0022856 | A1 | 1/2003 | Richardson et al. |
| 2003/0026844 | A1 | 2/2003 | Lee et al. |
| 2003/0129178 | A1 | 7/2003 | Wegman et al. |
| 2004/0137596 | A1 | 7/2004 | Kurfuerst et al. |
| 2005/0227910 | A1 | 10/2005 | Yang et al. |
| 2005/0261584 | A1 | 11/2005 | Eshel et al. |
| 2005/0267080 | A1 | 12/2005 | Kolodney et al. |
| 2006/0204488 | A1 | 9/2006 | Badalamente |
| 2006/0251581 | A1 | 11/2006 | McIntyre et al. |
| 2007/0003541 | A1 | 1/2007 | Faudoa et al. |
| 2007/0031482 | A1 | 2/2007 | Castro et al. |
| 2007/0224183 | A1 | 9/2007 | Sabatino et al. |
| 2007/0224184 | A1 | 9/2007 | Badalemente et al. |
| 2008/0020001 | A1 | 1/2008 | Brehm et al. |
| 2008/0206228 | A1 | 8/2008 | Vaccaro et al. |
| 2008/0233614 | A1 | 9/2008 | Cranenburgh et al. |
| 2008/0279900 | A1 | 11/2008 | Longo et al. |
| 2008/0300429 | A1 | 12/2008 | Sakanishi et al. |
| 2009/0053276 | A1 | 2/2009 | Richard |
| 2010/0015262 | A1 | 1/2010 | Goralczyk et al. |
| 2010/0021416 | A1 | 1/2010 | Lichter et al. |
| 2010/0035868 | A1 | 2/2010 | Jabbour |
| 2010/0086971 | A1 | 4/2010 | Suppmann et al. |
| 2010/0137747 | A1 | 6/2010 | Thomas et al. |
| 2010/0159564 | A1 | 6/2010 | Dwulet et al. |
| 2010/0233150 | A1 | 9/2010 | Wegman et al. |
| 2010/0233151 | A1 | 9/2010 | Sabatino et al. |
| 2011/0158972 | A1 | 6/2011 | Sabatino et al. |
| 2011/0160617 | A9 | 6/2011 | Thomas et al. |
| 2011/0189153 | A1 | 8/2011 | Sabatino et al. |
| 2011/0189163 | A1 | 8/2011 | Sabatino et al. |
| 2011/0217252 | A1 | 9/2011 | Koverech |
| 2011/0243908 | A1 | 10/2011 | Sabatino et al. |
| 2011/0243909 | A1 | 10/2011 | Sabatino et al. |
| 2011/0243919 | A1 | 10/2011 | Sabatino et al. |
| 2011/0243920 | A1 | 10/2011 | Sabatino et al. |
| 2011/0262508 | A1 | 10/2011 | Watt et al. |
| 2011/0294192 | A1 | 12/2011 | Fukushima et al. |
| 2012/0164131 | A1 | 6/2012 | Huang et al. |
| 2012/0237492 | A1 | 9/2012 | Walker |
| 2012/0237497 | A1 | 9/2012 | Wegman et al. |
| 2012/0315265 | A1 | 12/2012 | Lai et al. |
| 2013/0096596 | A1 | 4/2013 | Schafer |
| 2013/0129663 | A1 | 5/2013 | Friberg et al. |
| 2013/0195828 | A1 | 8/2013 | Kibbe et al. |
| 2013/0197397 | A1 | 8/2013 | Waugh et al. |
| 2013/0217789 | A1 | 8/2013 | Taylor et al. |
| 2013/0287759 | A1 | 10/2013 | Ramon |
| 2014/0004094 | A1 | 1/2014 | Sabatino et al. |
| 2014/0271508 | A1 | 9/2014 | Florence et al. |
| 2014/0271612 | A1 | 9/2014 | Leppert et al. |
| 2014/0335072 | A1 | 11/2014 | Hart |
| 2015/0301064 | A1 | 10/2015 | Yoshida et al. |
| 2016/0000890 | A1 | 1/2016 | Yu et al. |
| 2016/0279046 | A1 | 9/2016 | Badalemente et al. |
| 2017/0136039 | A1 | 5/2017 | Jung et al. |
| 2017/0209201 | A1 | 7/2017 | Slayton et al. |
| 2017/0228517 | A1 | 8/2017 | Saliman et al. |
| 2017/0290848 | A1 | 10/2017 | Walker |
| 2017/0319601 | A1 | 11/2017 | Walker |
| 2019/0240253 | A1 | 8/2019 | Abst et al. |
| 2021/0220284 | A1 | 7/2021 | Leppert et al. |

FOREIGN PATENT DOCUMENTS

| | | |
|---|---|---|
| CA | 2308842 A1 | 12/2000 |
| CA | 2643171 A1 | 9/2007 |
| EP | 0468411 A2 | 1/1992 |
| EP | 0748608 A1 | 12/1996 |
| EP | 1433845 A1 | 6/2004 |
| EP | 2130551 | 12/2009 |
| EP | 2133415 A1 | 12/2009 |
| EP | 2180002 A1 | 4/2010 |
| EP | 2363461 A1 | 9/2011 |
| FR | 2788682 A1 | 7/2000 |
| JP | 05-219942 A | 8/1993 |
| JP | 06-237764 A | 8/1994 |
| JP | 10-262658 A | 10/1998 |
| JP | 2002-530873 A | 9/2002 |
| JP | 2003-284553 A | 10/2003 |
| JP | 2004-535197 A | 11/2004 |

(56) References Cited

FOREIGN PATENT DOCUMENTS

| | | |
|---|---|---|
| JP | 2005-006552 A | 1/2005 |
| JP | 3122177 U | 6/2006 |
| JP | 2006-254876 A | 9/2006 |
| JP | 2011-528716 A | 11/2011 |
| JP | 2014-530873 A | 11/2014 |
| JP | 2015-506247 A | 3/2015 |
| JP | 2015-134840 A | 7/2015 |
| JP | 2016-135760 A | 7/2016 |
| RU | 2180002 C2 | 2/2002 |
| WO | 94/00580 A1 | 1/1994 |
| WO | 96/00283 A1 | 1/1996 |
| WO | 96/28543 A1 | 9/1996 |
| WO | 98/24889 A1 | 6/1998 |
| WO | 00/30182 A2 | 5/2000 |
| WO | 01/21574 A1 | 3/2001 |
| WO | 03/04628 A2 | 1/2003 |
| WO | 2004/085643 A1 | 10/2004 |
| WO | 2005/073367 A1 | 8/2005 |
| WO | 2005/123764 A1 | 12/2005 |
| WO | 2006/002646 A2 | 1/2006 |
| WO | 2006/010057 A2 | 1/2006 |
| WO | 2006/025226 A1 | 3/2006 |
| WO | 2006/078870 A2 | 7/2006 |
| WO | 2006/121968 A2 | 11/2006 |
| WO | 2007/089851 A2 | 8/2007 |
| WO | 2007/100590 A2 | 9/2007 |
| WO | 2007/100675 A2 | 9/2007 |
| WO | 2008/101406 A1 | 8/2008 |
| WO | 2010/011605 A2 | 1/2010 |
| WO | 2011/073925 A2 | 6/2011 |
| WO | 2011/130537 A2 | 10/2011 |
| WO | 2012/031245 A1 | 3/2012 |
| WO | 2012/041512 A1 | 4/2012 |
| WO | 2012/125948 A1 | 9/2012 |
| WO | 2013/059619 A1 | 4/2013 |
| WO | 2015/108901 A1 | 7/2015 |
| WO | 2018/160905 A1 | 9/2018 |
| WO | 2018/183582 A2 | 10/2018 |

OTHER PUBLICATIONS

Endo, "Endo Announces Positive Data from Phase 2b Study of Collagenase Clostridium Histolyticum (CCH) in Patients with Cellulite", published on Nov. 17, 2016 (Year: 2016).*
Bielfeldt, "Non-invasive evaluation techniques to quantify the efficacy of cosmetic anti-cellulite products", Skin Research and Technology, published in 2008 (Year: 2008).*
Hamzeh Alipour et al., "Therapeutic applications of collagenase (metalloproteases): A review", pub. Jul. 17, 2016 (Year: 2016).*
Doris Hexsel et al., , "Cellulite: Classification and Scoring", pub. 2015 (Year: 2015).*
Bielfeldt et al., No-invasive evaluation techniques to qualify the efficacy of cosmetic anti-cellulite products, Skin Research and Technology, pub. in 2008, (Year: 2008).*
To Doris Hexsel et al., "Cellulite: Classification and Scoring", pub.2015 (Year: 2015).*
Smalls, "Effect of Weight Loss on Cellulite: Gynoid Lypodystrophy", Plast. Reconstr. Surg., 2006, vol. 118, No. 2, pp. 510-516.
Smalls, "Quantitative Model of Cellulite: Three-Dimensional Skin Surface Topography, Biophysical Characterization, and Relationship to Human Perception", J. Cosmet. Sci., Mar./Apr. 2005, pp. 105-120.
Smith et al., "A multicenter, double-blind, placebo-controlled trial of autologous fibroblast therapy (Azficel-T) for the treatment of nasolabial fold wrinkles", Dermatol. Surg., 2012, vol. 38, No. 7, pp. 1234-1243.
Strömberg et al., "Comparison of Treatment Outcome After Collagenase and Needle Fasciotomy for Dupuytren Contracture: A Randomized, Single-Blinded, Clinical Trial With a 1-Year Follow-Up", J. Hand Surg. Am., 2016, vol. 41, No. 9, pp. 873-880.

Strömberg et al., "Percutaneous Needle Fasciotomy Versus Collagenase Treatment for Dupuytren Contracture, A Randomized Controlled Trial with a Two-Year Follow-up", J. Bone Joint Surg. Am., 2018, vol. 100, pp. 1079-1086.
Tay et al., "Comparison between Collagenase Injection and Partial Fasciectomy in the Treatment of Dupuytren's Contracture", Hand Surg. 2015, vol. 20, No. 3, pp. 386-390.
TeensHealth, "Cellulite", TeensHealth.org, reviewed May 2009, 2 pages.
Thomas et al., "The Emerging Role of Clostridium histolyticum Collagenase in the Treatment of Dupuytren Disease", Ther. Clin. Risk Manag., 2010, vol. 6, pp. 557-572.
Tonkin, "Classification of Congenital Anomalies of the Hand and Upper Limb", J. Hand Surg. Am., 2015, vol. 40, No. 2, pp. 415-416.
U.S. Department of Health and Human Services, Food and Drug Administration, Center for Drug Evaluation and Research (CDER), Center for Biologics Evaluation and Research (CBER),Center for Devices and Radiological Health (CDRH), Guidance for Industry, Patient-Reported Outcome Measures: Use in Medical Product Development to Support Labeling Claims, Clinical/Medical, Dec. 2009, pp. 1-43.
Vos-Scheperkeuter et al., "Histochemical Analysis of the Role of Class I and Class II Clostridium Istochemical Analysis of the Role Histolyticum Collagenase in the Degradation of Rat Pancreatic Extracellular Matrix for Islet Isolation", Cell Transplantation, 1997, vol. 6, pp. 403-412.
Waters et al., "Collagenase Enzymatic Fasciotomy for Dupuytren Contracture in Patients on Chronic Immunosuppression", Am. J. Orthop., 2015, vol. 44, No. 11, pp. 518-521.
Wikipedia.org "Cellulite," http://en.wikipedia.org/wiki/cellulite, Dec. 15, 2012, pp. 1-5.
Xiaflex(Registered), Collagenase clostridium histolyticum, Prescribing Information, Revised Nov. 2019, Malvern, PA: Endo Pharmaceuticals Inc.
Young et al., "Comparisons of Clinician-Reported and Patient-Reported Cellulite Severity Scales with existing scales for measurement of cellulite severity", Podium presented at the 34th Annual Meeting of the Northeastern Society of Plastic Surgeons (NESPS 2017), Sep. 8-10, 2017.
Young et al., "Efficacy and safety of collagenase clostridium histolyticum for the treatment of edematous fibrosclerotic panniculopathy (cellulite)", Podium presented at the American Society of Plastic Surgeons Aesthetica 2017 Super Symposium, Mar. 2-4, 2017, New Orleans, LA.
Zhou et al., "Collagenase Clostridium Histolyticum versus Limited Fasciectomy for Dupuytren's Contracture", Plast. Reconstr. Surg., 2015, vol. 136, No. 1, pp. 87-97.
Goldstein et al., "Impact of Collagenase Clostridium Histolyticum Treatment of Men With Peyronie's Disease on Improvement of Female Partner Sexual Function", AUA 2018.
Goldstein et. al., "Changes in the Effects of Peyronie's Disease After Treatment With Collagenase Clostridium histolyticum: Male Patients and Their Female Partners", Sex Med., Jun. 2017, vol. 5, No. 2, pp. e124-e130.
Hale et. al., "Long-term safety and analgesic efficacy of buprenorphine buccal film in patients with moderate-to- severe chronic pain requiring around-the-clock opioids", J. Pain Res., 2017, vol. 10, pp. 233-240.
Harmon, "Is Cellulite Forever?", Scientific American, Monday, May 4, 2009, vol. 56, pp. 1-4.
Hay et al., "Surgical findings in the treatment of Dupuytren's disease after initial treatment with clostridial collagenase (Xiaflex)", J. Hand Surg. Eur., 2014, vol. 39,No. 5, pp. 463-465.
Hellstrom et al., "Safety Profile of Collagenase Clostridium Histolyticum Stratified by Degree of Penile Curvature in Patients With Peyronie Disease", Urology, Aug. 2017, vol. 106, pp. 237.e9-237.e14.
Hexsel et al., "Noninvasive treatment of cellulite utilizing an expedited treatment protocol with a dual wavelength laser-suction and massage device", Journal of Cosmetic and Laser Therapy, 2013, vol. 15, pp. 65-69.
Hexsel et al., "A validated photonumeric cellulite severity scale", JEADV 2009, vol. 23, pp. 523-528.

(56) References Cited

OTHER PUBLICATIONS

Hurst et al., "Injectable Collagenase Clostridium Histolyticum for Dupuytren's Contracture", N. Engl. J. Med., 2009, vol. 361, No. 10, pp. 968-979.

Hutchinson et al., "Dupuytren's Disease and Frozen Shoulder Induced by Treatment with a Matrix Metalloproteinase Inhibitor", The Journal of Bone and Joint Surgery, 1998, vol. 80B, No. 5, pp. 907-908.

Imhof, "A Phase III Study of IncobotulinumtoxinA in the Treatment of Glabellar Frown Lines", J. Clin. Aesthet. Dermatol., 2011, vol. 4, No. 10, pp. 28-34.

Information Related to ClinicalTrials.gov Identifier: NCT01518907; "The Safety, Effectiveness, and Pharmacokinetics of AA4500 for the Treatment of Edematous Fibrosclerotic Panniculopathy (Commonly Known as Cellulite)", Jan. 26, 2012, pp. 1-9, from: https://clinicaltrials.gov/ct2/show/NCT01518907.

Kaminer et al., "Validated Assessment Scales for Skin Laxity on the Posterior Thighs, Buttocks, Anterior Thighs, and Knees in Female Patients", Dermatologic Surgery, Aug. 2019, vol. 45, pp. S12-S21.

Kaplan et al., "Predictors of recurrence for joints successfully treated with collagenase clostridium histolyticum injections", Podium presented at the 39th Annual Meeting of the American Society for Hand Therapists (ASHT 2016), Sep. 15-18, 2016, pp. 1-3.

Kirby et al., "Assessing cellulite severity: method for assessing reliability of a new clinician-reported and a new patient-reported photonumeric scale", Poster presented at the International Society of Pharmacoeconomics and Outcomes Research (ISPOR 2018), May 19-23, 2018.

Kirby et al., "Assessing Cellulite Severity: Test-Retest Reliability of and Concordanance Between New Clinician Reported and Patient Reported Photonumeric Scales", PS 2018.

McLane et al., "Analysis of Potential Impact of Healthcare Provider Gender on Rating Cellulite Severity", ASPS, Mar. 1-3, 2018, 3 pages.

McLane et al., "Analysis of Potential Impact of Healthcare Provider Gender on Rating Cellulite Severity", Sep. 28-Oct. 2018, 4 pages.

McLane et al., "Assessing Cellulite Severity: Test-Retest Reliability of and Concordanance Between New Clinician Reported and Patient Reported Photonumeric Scales", ASPS 2018.

McMahon et al., "Pharmacokinetics, Clinical Efficacy, Safety Profile, and Patient-Reported Outcomes in Patients Receiving Subcutaneous Testosterone Pellets 900 mg for Treatment of Symptoms Associated With Androgen Deficiency", J. Sex Med., Jul. 2017, vol. 14, No. 7, pp. 883-890.

MedlinePlus, "Cellulite", http://www.nlm.nih.gov/medlineplus/ency/article/002033.htm, pp. 1-2, updated Oct. 10, 2010.

Muppavarapu et al., "Clinical outcomes following collagenase injections compared to fasciectomy in the treatment of Dupuytren's contracture", Hand, 2015, vol. 10, No. 2, pp. 260-265.

Naam, "Functional outcome of collagenase injections compared with fasciectomy in treatment of Dupuytren's contracture", Hand (NY), 2013, vol. 8, No. 4, pp. 410-416.

Narins et al., "A randomized, double-blind, multicenter comparison of the efficacy and tolerability of restylane versus zyplast for the correction of nasolabial folds", Dermatol. Surg., 2003, vol. 29, No. 6, pp. 588-595.

National Library of Medicine, "MeSH Descriptor Data—Hyaluronoglucosaminidase", http://www.nlm.nih.gov/cgi/mesh/2008/MB_cgi?mode=&term=hyaluronidase, 2008, 1 page.

Nurnberger et al., "So-called Cellulite: An Invented Disease", J. Dermatol. Surg. Oncol. 1978, vol. 4, pp. 221-229.

Nydick et al., "A comparison of percutaneous needle fasciotomy and collagenase injection for dupuytren disease", J. Hand Surg. Am., 2013, vol. 38, No. 12, pp. 2377-2380.

OBGYN.Net Headline News, "Successful phase II results lead to phase III approval-Dupuytren disease", Posted at the web on Oct. 8, 2001, (at the web: http://www.obgyn.net/newsrx/general_health-dupuytren_disease-20011008-21.asp), especially pp. 1-2, last paragraph.

Peimer et al., "Dupuytren contracture recurrence following treatment with collagenase clostridium histolyticum (Cordless [Collagenase Option for Reduction of Dupuytren Long-Term Evaluation of Safety Study]): 5-year data", J. Hand Surg. Am., 2015, vol. 40, No. 8, pp. 1597-1605.

Povlsen et al., "What is the better treatment for single digit dupuytren's contracture: surgical release or collagenase clostridium histolyticum (Xiapex) injection?", Hand Surg., 2014, vol. 19, No. 3, pp. 389-392.

Press Release, "Auxilium Pharmaceuticals, Inc. Announces First Patients Dosed in Xiaflex Phase Ib Cellulite Study", Jan. 26, 2012; 1 page; downloaded from: http://phx.corporate-ir.net/phoenix.zhtml?c=142125&p=irol-newsArchiveArticle&ID=1653001.

Press Release, "Auxilium Pharmaceuticals, Inc. Announces First Patients Dosed in Xiaflex Phase Ib Cellulite Study", Jan. 26, 2011, 4 pages; downloaded from: https://www.sec.gov/Archives/edgar/data/1182129/000119312512024205/d290313dex991.htm.

Press Release, PRNewswire, "Auxilium Pharmaceuticals, Inc. Announces First Patients Dosed in Xiaflex Phase IB Cellulite Study", Jan. 26, 2012, 7 pages, downloaded from: https://www.prnewswire.com/news-releases/auxilium-pharmaceuticals-inc-announces-first-patients-dosed-in-xiaflex-phase-ib-cellulite-study-138113223.html.

Press Releases, "Endo Announces Positive Results from Phase 3 Studies of Collagenase Clostridium Histolyticum (CCH) in Patients with Cellulite", Nov. 7, 2018, pp. 1-3.

Priestley et al., "Converting from Transdermal to Buccal Formulations of Buprenorphine: A Pharmacokinetic Meta-Model Simulation in Healthy Volunteers", Pain Med., Oct. 1, 2018, vol. 19, No. 10, pp. 1988-1996.

Ralph et al., "Collagenase clostridium histolyticum in combination with vacuum therapy in patients with Peyronie's disease", Podium presented at the 22nd Annual Fall Scientific Meeting of the Sexual Medicine Society of North America (SMSNA 2016), Nov. 2016, 1 page.

Ralph et al., "The safety and efficacy of collagenase clostridium histolyticum (CCH) in combination with vacuum therapy for the treatment of Peyronie's disease", SMSNA 2016.

Ralph et al., "The safety and efficacy of collagenase clostridium histolyticum in combination with vacuum therapy for the treatment of Peyronie's disease", Podium presented at the 112th Annual Meeting of the American Urological Association (AUA 2017), May 12-16, 2017, Boston, MA.

Ralph et. al., "Treatment of Peyronie's Disease With Collagenase Clostridium histolyticum and Vacuum Therapy: A Randomized, Open-Label Pilot Study", J. Sex Med., Nov. 2017, vol. 14, No. 11, pp. 1430-1437.

Sadick et al., "Comparisons of Clinical Reported and Patient Reported Cellulite Severity Scales With Existing Scales for Measurement of Cellulite Severity", Maui Derm, 2018.

Sadick et al., "Efficacy and Safety Evaluation of Collagenase Clostridium Histolyticum for the Treatment of Edematous Fibrosclerotic Panniculopathy (Cellulite)", Poster presented at the 2017 American Society for Dermatologic Surgery Annual Meeting (ASDS 2017); Oct. 5-8, 2017, Chicago, IL.

Sadick et al., "Efficacy and Safety Evaluation of Collagenase Clostridium Histolyticum for the Treatment of Edematous Fibrosclerotic Panniculopathy", Poster presented at the Maui Derm For Dermatologist 2018, Jan. 28-Feb. 1, 2018.

Sadick, "Collagenase Clostridium Histolyticum for the Treatment of Edematous Fibrosclerotic Panniculopathy", VCS 2018.

Sadick, "New measurement and treatment options for edematous fibrosclerotic panniculopathy (cellulite): results from a randomized, double-blind, placebo-controlled trial of CCH", Podium presented by Dr. John Joseph at the Vegas Cosemetic Surgery (VCS), Jun. 6-10, 2018, Las Vegas, NV, VCS 2018.

Sasaki., "Single Treatment of Grades II and III Cellulite Using a Minimally Invasive 1,440-nm Pulsed Nd:YAG Laser and Side-Firing Fiber: An Institutional Review Board-Approved Study with a 24-Month Follow-Up Period", published on Oct. 11, 2013, vol. 37, pp. 1073-1089.

Scherman et al., "One-year results of needle fasciotomy and collagenase injection in treatment of Dupuytren's contracture: A two-

(56) References Cited

OTHER PUBLICATIONS centre prospective randomized clinical trial", J. Hand Surg. Eur., 2016, vol. 41, No. 6, pp. 577-582.
Serefoglu et.al., "Factors Associated With Erectile Dysfunction and the Peyronie's Disease Questionnaire in Patients With Peyronie Disease", Urology, Sep. 2017, vol. 107, pp. 155-160.
Siegel et al., "Adhesive Capsulitis: A Sticky Issue", American Family Physician, 1999, vol. 59, No. 7, pp. 1843-1852.
Skov et al., "Injectable Collagenase Versus Percutaneous Needle Fasciotomy for Dupuytren Contracture in Proximal Interphalangeal Joints: A Randomized Controlled Trial", J. Hand Surg. Am., 2017, vol. 42, No. 5, pp. 321-328.
Smalls, "Development of Quantitative Modes for the Investigation of Gynoid Lipodystrophy (Cellulite)", Ph.D. Thesis, University of Cincinnati, 2005, pp. 1-210.
Aldrich, "Collagenase Guide", Feb. 10, 2005, pp. 1-4.
Almeida et al., "Intra- and inter-observer reliability of the application of the cellulite severity scale to a Spanish female population : CSS reliability in a Spanish female population", Jeadv. Journal of the European Academy of Dermatology and Venereology., Apr. 6, 2012, vol. 27, No. 6, pp. 694-698.
Almeida et al., "Reliability of texture analysis using co-occurrence matrices (glcm) on photographic image in the assessment of cellulite in a Spanish population", Journal of the European Academy of Dermatology and Venerology, Feb. 2015, vol. 29, No. 2, pp. 315-324.
Atroshi et al., "Costs for collagenase injections compared with fasciectomy in the treatment of Dupuytren's contracture: a retrospective cohort study", BMJ Open, 2014, vol. 4, No. 1, e004166, pp. 1-7.
Australian Public Assessment Report for Collagenase clostridium histolyticum, Australian Government, Department of Health, Therapeutic Goods Administration, Proprietary Product Name: Xiaflex, Sponsor: Actelion Pharmaceuticals Australia Pty Ltd, Nov. 2013, pp. 1-83.
Auxilium et al., "Auxilium Pharmaceuticals, Inc. Announces First Patients Dosed in Xiaflex Phase lb.", Cellulite Study, Jan. 26, 2011, pp. 1-7.
Badalamente et al., "Collagen as a clinical target: Nonoperative treatment of dupuytren's disease", The Journal of Hand Surgery, W.B. Saunders, Sep. 1, 2002, vol. 27, No. 5, pp. 788-798.
Badalamente et al., "Efficacy and Safety of Injectable Mixed Collagenase Subtypes in the Treatment of Dupuytren's Contracture", The J. of Hand Surgery, 2007, vol. 32A, No. 6, pp. 767-774.
Balci et al., "Shoulder Adhesive Capsulitis and shoulder range of motion in Type II Diabetes Mellitus: association with diabetic complications", Journal of Diabetes and its Complications, Elsevier Science, New York, NY, Jan. 1, 1999, vol. 13, pp. 135-140.
Ballard et al., "Purification and Characterization of the Lethal Toxin (Alpha-Toxin) of Clostridium Septicum", Infection and Immunity, 1990, vol. 60, No. 3, pp. 784-790.
Bauer, "Endo Announces Positive Data from Phase 2b Study of Collagenase Clostridium Histolyticum (CCH) in Patients with Cellulite", Endo International plc, Nov. 17, 2016, vol. 8, No. 30, pp. 1-30.
Bauer, "Non-contact thermal imaging as potential tool for personalized diagnosis and prevention of cellulite", 2018, vol. 133, pp. 571-578.
Bear et al., "Treatment of Recurrent Dupuytren Contracture in Joints Previously Effectively Treated with Collagenase Clostridium Histolyticum", J. Hand Surg. Am., 2017, vol. 42, No. 5, pp. 391.e1-391.e8.
Bielfeldt et al., "Non-invasive evaluation techniques to quantify the efficacy of cosmetic anti-cellulite products", Skin Research and Technology, 2008, vol. 14, pp. 336-346.
Billington et al., "Thiol-Activated Cytolysins: Structure, Function and Role in Pathogenesis", FEMS Microbiol. Lett., 2000, vol. 182, No. 2, pp. 197-205.
Bonnerjea et al., "Protein purification: the right step at the right time", Biotechnology, Nov. 1986, vol. 4, pp. 954-958.
Bowen, "A Comparison of the Lethal and Hemolytic Toxins of Clostridium Histolyticum", J. Biol. Med., 1952, vol. 25, No. 2, pp. 124-138.
Brandt et al., "Safety and Effectiveness of Small and Large Gel-Particle Hyaluronic Acid in the Correction of Perioral Wrinkles", J. Drugs Dermatol., 2011, vol. 10, No. 9, pp. 982-987.
Brunengraber et al., "Injectable Clostridium Histolyticum Collagenase as a Potential Treatment for Uterine Fibroids", Reproductive Sciences, 2014, vol. 21, No. 12, pp. 1452-1459.
Bunker et al., "The pathology of frozen shoulder. A Dupuytren-like disease", The Journal of Bone and Joint Surgery, British Volume, Sep. 1995, vol. 77, No. 5, pp. 677-683.
Bunker, "Frozen shoulder: unravelling the enigma", Ann R. Coll. Surg. Engl., 1997, vol. 79, pp. 210-213.
Callaghan et al., "Seminars in Cutaneous Medicine and Surgery, Cellulite: a review of pathogenesis-directed therapy", Dec. 2017, vol. 36, pp. 179-184.
Camper et al., "Cost per episode of care with collagenase clostridium histolyticum versus fasciectomy for Dupuytren's contracture: a real-world claims database analysis", Journal of Hand Surgery Global Online, 2019, pp. 57-64.
Center for Drug Evaluation and Research, Application No. 206330rig1s000; Other Review(s); PMR/PMC Development Template; https://www.accessdata.fda.gov/drugsatfda_docs/nda/2015/206333Orig1s000OtherR.pdf; Last Updated Apr. 27, 2015.
Center Watch Staff, "Bio-Specifics Technologies announces positive data from phase lib cellulite study", Nov. 21, 2016, pp. 1-2.
Citation of Prior Art and Statements Under 35 U.S.C. 301 dated Dec. 23, 2019.
Cohen et al., "Development and Validation Clinician and Patient Reported Photonumeric Scales to Assess Buttocks Cellulite Severity", Dermatol. Surg., Dec. 2020, vol. 46, No. 12, pp. 1628-1635.
Collagenase, "Worthington Enzyme Manual available at http://www.worthington-biochem.com/cls/default.html", downloaded from internet on Dec. 1, 2020, pp. 1-4.
Coons et al., "Recommendations on Evidence Needed to Support Measurement Equivalence between Electronic and Paper-Based Patient-Reported Outcome (PRO) Measures: ISPOR ePRO Good Research Practices Task Force Report", Value in Health, 2009, vol. 12, pp. 419-429.
Costas et al., "A randomized phase 2A, double-blind, placebo-controlled, dose-ranging study to evaluate the safety and effectiveness of collagenase clostridium histolyticum (cch) in the treatment of Dupuytren disease nodules", Podium presented at the 71st Annual Meeting of the American Society for Surgery of the Hand (ASSH 2016), Sep. 29-Oct. 1, 2016, Austin, TX, pp. 1-2.
Costas et al., "Efficacy and safety of collagenase clostridium histolyticum for Dupuytren disease nodules: a randomized controlled trial", BMC Musculoskelet. Disord., Aug. 30, 2017, vol. 18, No. 374, pp. 1-10.
Cuggino et al., "Synthesis, characterization and slow drug delivery of hydrogels based in N-acryloyl-tris-(hydroxymethyl) aminomethane and N-isopropyl acrylamide", Reactive & Functional Polymers, 2011, vol. 71, pp. 2440-2446.
Demidyuk et al., "Structural Organization of Precursors of Thermolysin-like Proteinases", Protein J., 2008, vol. 27, pp. 343-354.
Divino et al., "Total cost of care associated with collagenase clostridium histolyticum versus fasciectomy for the treatment of Dupuytren's contracture: a retrospective cohort analysis", American Association for Hand Surgery (AAHS) Annual Meeting, 2018, pp. 1-3.
Draelos, "The disease of cellulite", Journal of Cosmetic Dermatology, Dec. 2005, vol. 4, Issue 4, pp. 1-3.
Ducka et al., "A universal strategy for high-yield production of soluble and functional clostridial collagenases in *E. coli*", Appl. Microbiol. Biotechnol., 2009, vol. 83, pp. 1055-1065.
Eckhard et al., "Structural Basis for Activity Regulation and Substrate Preference of Clostridial Collagenases G, H, and T", J. Biol. Chem., Jul. 12, 2013, vol. 288, No. 28, pp. 20184-20194.
Eddie Staley, "Auxilium Pharmaceuticals Announces First Patients Dosed in Xiaflex Phase Ib Cellulite Study", Jan. 26, 2012, 1 page

(56) References Cited

OTHER PUBLICATIONS downloaded from: https://www.benzinga.com/news/12/01/2291202/auxilium-pharmaceuticals-announces-first-patients-dosed-in-xiaflex-hase-ib-cellu.

Edkins et al., "Assessment of Potential Cross-Reactivity of Human Endogenous Matrix Metalloproteinases With Collagenase Clostridium Histolyticum Antibodies In Human Sera Obtained From Patients With Dupuytren's Contracture", Clinical And Vaccine Immunology, 2012, vol. 19, No. 4, pp. 562-569.

EMBL, "Protein Expression and Purification Core Facility", Cloning Choice of Expression Systems, 2002, pp. 1-4.

Food and Drug Administration, "Guidance for Industry on Patient-Reported Outcome Measures: Use in Medical Product Development to Support Labeling Claims", Availability Use in Medical Product Development to Support Labeling claims. Federal Register, 2009, vol. 74, No. 235, pp. 65132-65133.

Friedman et al., "Degradation of porcine dermal connective tissue by collagenase and hyaluronidase", British Journal of Dermatology, 1986, vol. 115, pp. 403-408.

Gaston et al., "The Efficacy and Safety of Concurrent Collagenase Clostridium Histolyticum Injections for 2 Dupuytren Contractures in the Same Hand: A Prospective, Multicenter study", J. Hand Surg. Am., 2015, vol. 40, No. 10, pp. 1963-1971.

Gilpin et al., "Injectable collagenase clostridium histolyticum: a new nonsurgical treatment for Dupuytren's disease", J. Hand Surg. Am., 2010, vol. 35, No. 12, pp. 2027-2038.

Giudicelli et al., "Influence of trypsin on lipolysis in human fat cells comparison with rat adipocytes", Biochimica et Biophysica, 1976, Acta, vol. 450, Issue 3, pp. 358-366.

Goldman et al., "Cellulite: A New Treatment Approach Combining Subdermal Nd: YAG Laser Lipolysis and Autologous Fat Transplantation", Aesthetic Surg. J., 2008, vol. 28, pp. 656-662.

Goldman et al., "Phase 2a, randomized, double-blind, placebo-controlled dose-ranging study of repeat doses of collagenase clostridium histolyticum for the treatment of edematous fibrosclerotic panniculopathy (cellulite)", J. Am. Acad. Dermatol., 2015, vol. 72, Suppl. 5, Abstract 1721, 1 page.

Goldstein et al., "Baseline severity of Peyronie's Disease Symptoms Predicts Improved Female Partner Burden Scores After Treatment with Collagenase Clostridium Histolyticum", Moderated poster presented at the Sexual Medicine Society of North America (SMSNA 2017), Oct. 26-29, 2017, pp. 1-6.

Goldstein et al., "Baseline severity of Peyronie's Disease Symptoms Predicts Improved Female Partner Burden Scores After Treatment with Collagenase Clostridium Histolyticum", Podium presented at the American Urological Association (AUA 2018), May 21, 2018, San Francisco, CA, pp. 1-10.

Goldstein et al., "Extent of female partner sexual function improvement in female partners of men with Peyronie's disease who received collagenase clostridium histolyticum", SMSNA 2017, pp. S41-S42.

Alexiades-Armenakas et al., "Unipolar radiofrequency treatment to improve the appearance of cellulite", Journal of Cosmetic and Laser Therapy, May 19, 2008, vol. 10, No. 3, pp. 148-153.

Dibernardo et al., "A multicenter study for a single, three-step laser treatment for cellulite using a 1440-nm Nd: YAG laser, a novel side-firing fiber, and a temperature-sensing cannula", Aesthetic Surgery Journal, May 1, 2013, vol. 33, No. 4, pp. 576-584.

Dibernardo et al., "A Multicenter Study for Cellulite Treatment Using a 1440-nm Nd:YAG Wavelength Laser with Side-Firing Fiber", Aesthetic Surgery Journal, vol. 36, No. 3, 2016, pp. 335-343.

* cited by examiner

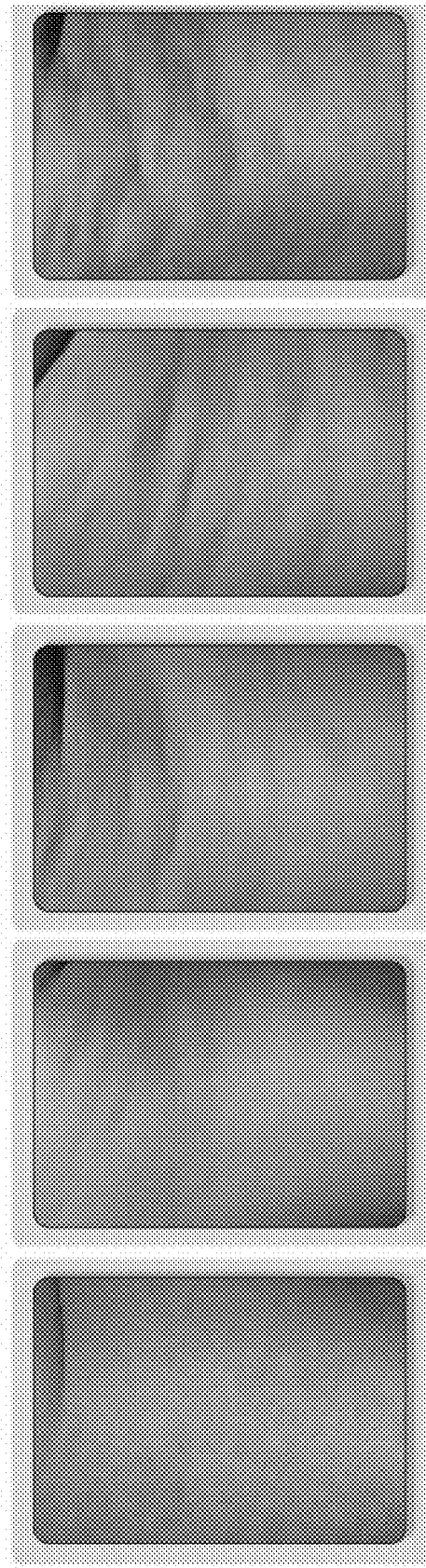

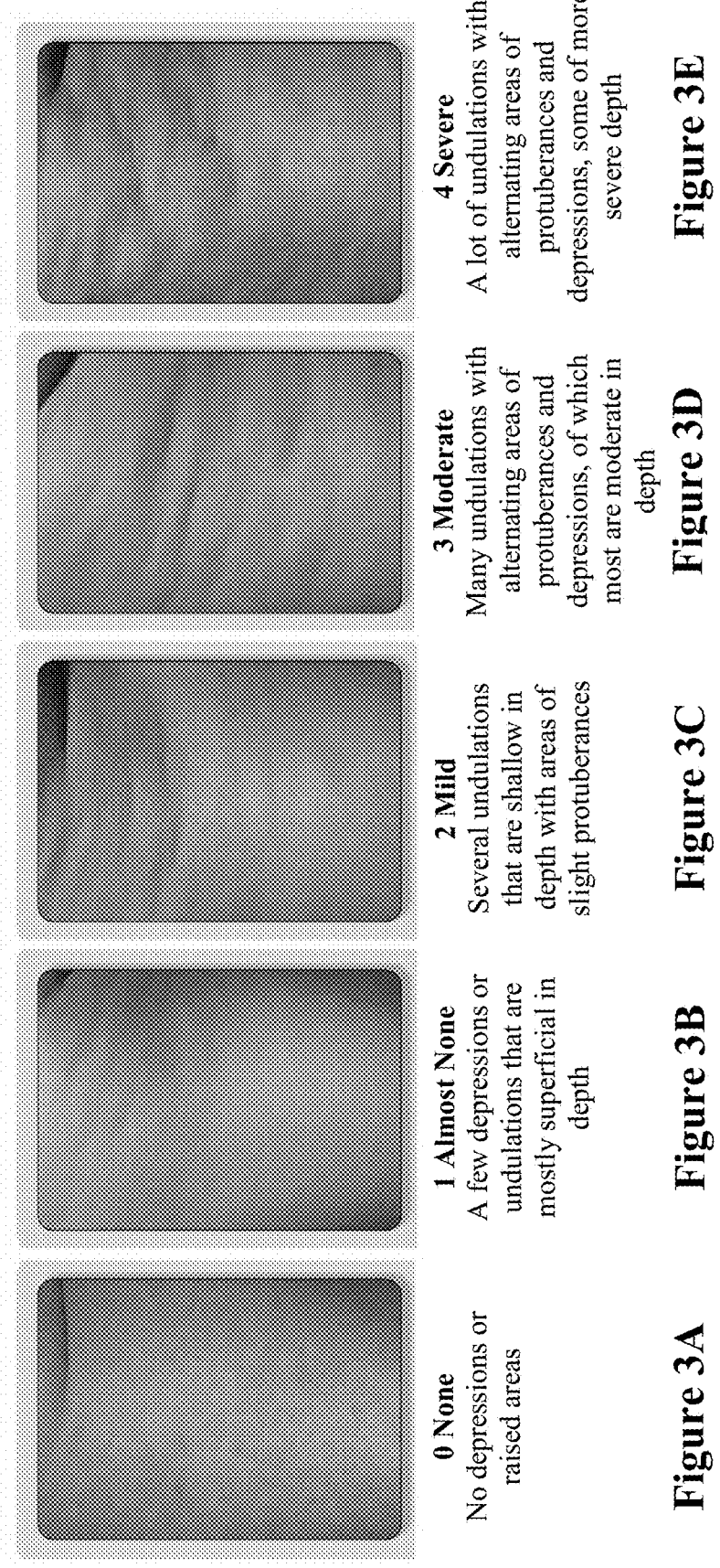

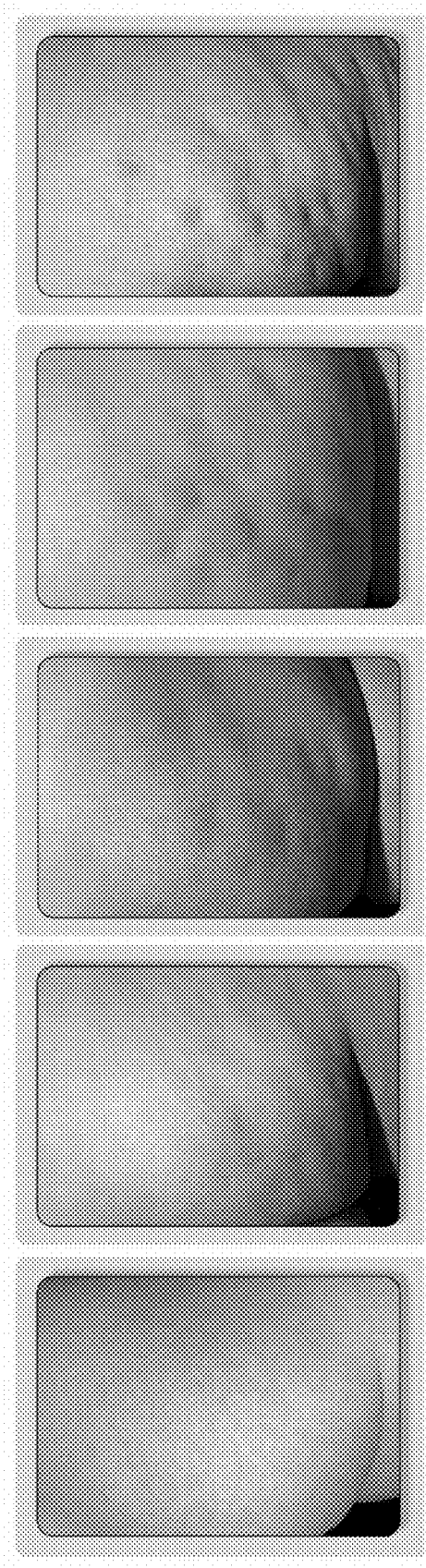

Figure 4A — 0 None — No evident cellulite
Figure 4B — 1 Almost None — A few superficial dimples or ridges
Figure 4C — 2 Mild — Several dimples or ridges of which most are superficial
Figure 4D — 3 Moderate — Many dimples or ridges of which most are somewhat deep
Figure 4E — 4 Severe — A lot of dimples or ridges of which many are deep covering most of the skin area Patient Reported Photonumeric Cellulite Severity Scale (PR-PCSS) – Buttock

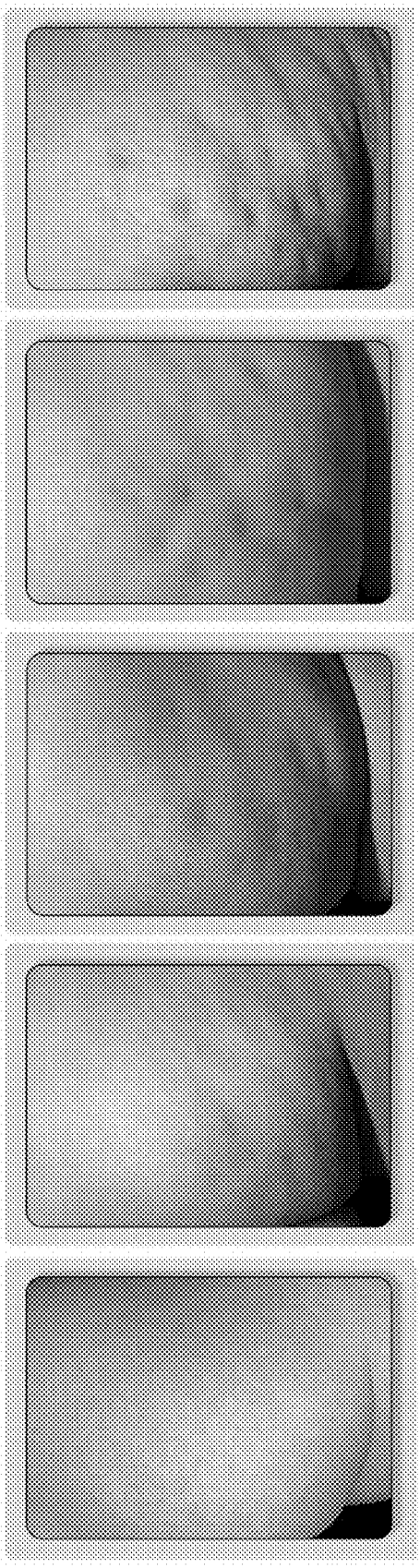

Clinician Reported Photonumeric Cellulite Severity Scale (CR-PCSS) – Buttock

| 0 None<br>No dimples or evident cellulite | 1 Almost None<br>Few dimples that are mostly superficial in depth | 2 Mild<br>Several dimples of which most are shallow in depth | 3 Moderate<br>Many dimples of which most are moderate in depth | 4 Severe<br>A lot of dimples with some of more severe depth |
|---|---|---|---|---|
| Figure 5A | Figure 5B | Figure 5C | Figure 5D | Figure 5E |

Day 1
Pre-treatment

Day 71
28 Days Following
Last Treatment

Day 1
Pre-treatment

Day 71
28 Days Following
Last Treatment

METHOD OF ASSESSING AND TREATING CELLULITE

RELATED APPLICATIONS

This application is a divisional application of U.S. patent application Ser. No. 17/461,481, filed on Aug. 30, 2021, which is a divisional of U.S. patent application Ser. No. 15/909,991, filed on Mar. 1, 2018, now U.S. Pat. No. 11,123,280, which claims priority to U.S. Provisional Application Ser. No. 62/465,622, filed on Mar. 1, 2017, U.S. Provisional Application Ser. No. 62/485,705, filed on Apr. 14, 2017, and U.S. Provisional Application Ser. No. 62/607,188, filed on Dec. 18, 2017, the contents of each of which are incorporated herein by reference in their entireties.

TECHNICAL FIELD

The present invention relates to the field of assessing and treating edematous fibrosclerotic panniculopathy (EFP or cellulite).

BACKGROUND

Edematous fibrosclerotic panniculopathy (EFP), commonly known as cellulite, has been defined as a local metabolic disorder of subcutaneous tissues that results in a contour abnormality of the skin. The condition manifests as dimpled skin, particularly in the gluteal-femoral region. EFP is caused by herniation of subcutaneous fat lobules through the dermohypodermal junction and/or shortening of the collagen septa that cross the hypodermal layer and connects the dermis to the underlying fascia. This creates an uneven surface with dimpling. EFP is a medical condition resulting in a potentially cosmetically unacceptable alteration of the skin, and affects an estimated 85% to 98% of postpubertal women.

The pathophysiology of EFP is not completely understood, but there are 3 main theories: edema resulting from excessive hydrophilia of the intercellular matrix, alteration of the regional microcirculation, and different anatomical conformation of collagenous subcutaneous tissues in women versus men.

It is known that EFP is different from generalized obesity. In generalized obesity, adipocytes undergo hypertrophy and hyperplasia that are not limited to the pelvis, thighs, and abdomen. In areas of EFP, adipocytes have physiologic and biochemical properties that differ from adipose tissue located elsewhere. Large, metabolically-stable adipocytes characterize EFP-prone areas; thus, the responsiveness to catecholamine-induced lipolysis is less in EFP tissues compared to visceral fat, which has the greatest responsiveness.

Subcutaneous fat lobes are separated from one another by thin, usually rigid strands of collagenous connective tissues, which cross the fatty layers and connect the dermis to the underlying fascia. These septa stabilize the subcutis and divide the fat. In EFP, shortening of the collagen septa due to fibrosis provokes retraction at the insertion points of the trabeculae, causing the depressions that characterize EFP. There are a higher percentage of thinner, perpendicular hypodermal septa in women with EFP than in men. Weight gain makes EFP more noticeable, but it may be present even in thin subjects. Genetics may also play a role since EFP tends to run in families.

There are therapies that have been utilized in an attempt to treat cellulite; however, there are no approved pharmacologic treatments. Despite multiple therapeutic modalities, there is little scientific evidence that any of these treatments are beneficial. In fact, much of the evidence is anecdotal, subjective, or based only on patient self-assessment. Some of the historical treatments for EFP have included weight loss, topical agents, massage, liposuction, mesotherapy, radiofrequency, subcision and powered subcision, and laser therapies; some of these treatments may pose an increased risk for adverse effects.

There remains an unmet need for safe and effective therapies to improve the aesthetic outcome in women with cellulite. To effectively treat cellulite, a therapeutic approach may require disruption of the dermal septa, which are composed of collagen and cause the skin dimpling that is bothersome to many women.

XIAFLEX® (collagenase *Clostridium histolyticum*, or CCH, or EN3835) is a biologic approved in the U.S., EU, Canada, Australia and Japan for the treatment of adult Dupuytren's contracture (DC) patients with a palpable cord and in the U.S. and EU for the treatment of adult men with Peyronie's disease (PD) with a palpable plaque and penile curvature deformity of at least 30 degrees at the start of therapy. XIAFLEX® (also known as XIAPEX in Europe) comprises a combination of two subtypes of collagenase, derived from *Clostridium histolyticum*. Together, the collagenase subtypes are thought to work synergistically to break the bonds of the collagen structure. A previous dose-ranging study in 150 women with EFP in the posterolateral thigh or buttock demonstrated that up to 3 injections of CCH 0.84 mg significantly improved EFP appearance versus placebo ($P<0.05$). Goldman M P, et al. J AM ACAD DERMATOL. 2015; 72(5 Suppl). Abstract 1721.

Treatment outcomes may be assessed by physicians and/or patients. To that end, the U.S. Food and Drug Administration (FDA) has published a Guidance for Industry: "*Patient-Reported Outcome Measures: Use in Medical Product Development to Support Labeling Claims*" (2009). It describes how FDA reviews and evaluates existing, modified, or newly created patient-reported outcome instruments used to support claims in approved medical product labeling.

The appearance of cellulite has been assessed in a number of ways using various photonumeric and other scales. Such scales include the Hexsel Cellulite Severity Scale "Hexsel CSS") and Global Aesthetic Improvement Scale ("GAIS"). The Hexsel CSS is described in Hexsel et al., "*A Validated Photonumeric Cellulite Severity Scale,*" J. EUR. ACAD. DERMATOL. Venereol. 2009 May; 23(5): 523-8. Briefly, the Hexsel CSS scores patients across five clinical morphologic features of cellulite: (A) the number of evident depressions; (B) depth of depressions; (C) morphological appearance of skin surface alterations; (D) grade of laxity, flaccidity or sagging skin; and (E) the classification scale originally described by Nürnberger and Müller (Nürnberger et al., "*So-called Cellulite: An Invented Disease,*" J. DERMATOL. SURG. ONCOL. 1978; 4:221-229. Using 20 separate photographs (i.e., 4 for each of the 5 morphological features), the severity of each item is graded from 0 to 3, and added together to provide a final sum of scores that range numerically from 0 to 15. Based on the final numeric score, cellulite was further classified as mild, moderate or severe.

While it was reported that the Hexsel CSS was reliable and consistent when used to evaluate cellulite on the buttocks and back of the thighs considered together, "the dimension grade of laxity, flaccidity or sagging skin does not contribute positively to the final consistency of the scale." Almeida et al., "*Infra- and inter-observer reliability of the application of the cellulite severity scale to a Spanish female*

*population*," J. EUR. ACAD. DERMATOL. VENEREOL., 2013 June; 27 (6): 694-8. Further, because of the number of steps required, the Hexsel CSS does not provide a concise means for assessment of cellulite severity. It is complex and relies on the user summing the results of multiple subcategories into a final score.

The GAIS is a 5-point scale rating global aesthetic improvement in appearance compared to pretreatment as judged by the investigator. Generally, unbalanced the rating categories are "worse," "no change," "improved," much improved," and "very much improved."

Thus, these scales of the prior art have a number of disadvantages, including a lack of accuracy from physician-to-physician and patient-to-patient. Accordingly, there is a need in the art for a reliable, consistent method for assessing, quantifying and rating the nature and extent of cellulite.

SUMMARY

The present disclosure satisfies the above need and relates to novel, validated scales useful in the diagnosis, assessment and treatment of cellulite. It further relates to methods of treating cellulite, in particular to the administration of a therapeutically effective amount of collagenase, obtained or derived from *Clostridium histolyticum* such as, e.g., XIA-FLEX®, to a subject in need thereof, and then assessing the extent of improvement using the novel scales. The scales of the present disclosure can be used with any therapeutic agent or treatment for cellulite (a) to establish a pre-treatment baseline; (b) during treatment to assess progress; or (c) post-treatment to evaluate the effect of therapy.

In one embodiment, the present disclosure provides a series of 3 to 15 photographs, illustrations, drawings, computer images, 3D models, MRI images, thermograms, ultrasonograms or the like each having a different cellulite severity rating or level. The scales are used by physicians/clinicians and patients. Efficacy of a particular collagenase treatment described herein may be based on a composite endpoint comprising the clinician rating and the patient rating where improvement is shown in both scales for the same subject, i.e., a pre-specified level of improvement is demonstrated in both the clinician and patent scales.

In another embodiment, the present disclosure describes a scale for assessing the severity of cellulite in a buttock or a thigh of a human subject, the scale comprising 3 to 10 photographs, illustrations, models, images, or drawings showing the buttock or thigh area of a human, the photographs, illustrations, models, images, or drawings being organized in different categories representing levels of severity based on a characteristic of cellulite; the characteristic being selected from the group consisting of the number and depth of dimples; and wherein when the scale is employed by a plurality of clinicians, at least 40% of the clinicians assign the subject's area of cellulite the same severity level. In certain embodiments, the clinicians provide the same severity level in at least 50% of the patients, or at least 60%, or at least 70%, or at least 80%, or at least 90% or about 100% of patients.

In another aspect, scales and methods are provided for performing clinical assessment of a patient that includes a baseline assessment by applying the scales of the present invention. The scales may comprise rows or columns of photographs corresponding to different severity categories. For example, a scale may include labels and word-based descriptions accompanying the rows of photographs corresponding to different severity categories. The word-based descriptions or labels may comprise the words: NONE, ALMOST NONE, MILD, MODERATE, and SEVERE. Such words are followed by explanatory words describing one or more features commonly found in the rows of photographs indicating the severity category.

In a further embodiment, the present disclosure is to validated, 5-point photonumeric scales, such as a Clinician Reported Photonumeric Cellulite Severity Scale (CR-PCSS) and a Patient Reported Photonumeric Cellulite Severity Scale (PR-PCSS). See FIGS. 2A-E, 3A-E, 4A-E, 5A-E. These photonumeric scales are designed to quantify the severity of cellulite into 5 levels. These validated CR-PCSS and PR-PCSS scales are particularly suitable (a) to establish a pre-treatment baseline; (b) during treatment to assess progress; or (c) post-treatment to evaluate the effect of therapy.

In using the scale, a clinician or patient compares one quadrant (left buttock, right buttock, left posterolateral thigh, or right posterolateral thigh), also known as treatment area of the patient to the pictures, labels, and descriptors on the CR-PCSS (see FIGS. 3 and 5 for clinicians) or PR-PCSS (see FIGS. 2 and 4 for patients), and match the patient's cellulite condition to one of the levels of severity on the CR-PCSS or PR-PCSS. The five severity levels are NONE, ALMOST NONE, MILD, MODERATE, and SEVERE. Separate scales are designed for the evaluation of the buttock and the evaluation of the thigh; both use the same 5-point severity levels, but with different descriptions tailored to each area.

There is also disclosed a method of assessing severity of cellulite in a human subject, comprising: (a) Selecting an affected area of thigh or buttock to evaluate; (b) comparing the affected area of the thigh or buttock to a series of photographs each with corresponding numbers as described in FIGS. 2 to 5; (c) identifying the photograph closest in appearance to the affected area of the thigh or buttock; (d) reading the number corresponding to the identified photograph; (e) identifying the label closest in appropriateness to the thigh or buttock or affected area of thigh or buttock; wherein utilizing the scales produces a consistency among evaluators of at least 50%.

In some embodiments, when the method using the CR-PCSS scale is employed by a plurality of clinicians, at least 40% of the clinicians give the patient's area of cellulite the same cellulite severity rating from when the patients were screened and Day 1 pre-treatment. Or, in other embodiments, clinicians provide such same rating in about 50%, or about 60%, or about 70%, or about 80%, or about 90% or about 100% of patients.

There is also disclosed a method for the treatment or alleviation of cellulite in a patient in need thereof, comprising: (a) assessing the severity of the patient's cellulite by using one or more validated scales to establish a baseline; (b) injecting a therapeutically effective amount of CCH to an affected area of a patient's thigh or buttock; and (c) evaluating the improvement resulting from such injection by using the one or more validated scales.

In one aspect, the amount of CCH injected is about 0.01 mg to 2 mg per treatment session in one or more injections. Any suitable collagenase composition may be used in the present invention. There may be 1 to 8 treatment sessions that occur about 10 to 60 days apart.

In another embodiment, patients receiving collagenase treatment have a ≥2-point improvement from baseline for both the CR-PCSS and PR-PCSS score at about 71 days after treatment, or have a ≥1-point improvement from baseline for both the CR-PCSS and PR-PCSS score at about 71 days post-treatment. Such patients have a ≥2-point improvement from baseline for both the CR-PCSS and PR-PCSS score at about 6 months after treatment, or have a ≥1-point improvement from baseline for both the CR-PCSS and PR-PCSS score at about 6 months post-treatment, or have a ≥2-point improvement from baseline for both the CR-PCSS and PR-PCSS score at about 12 months after treatment, or have a ≥1-point improvement from baseline for both the CR-PCSS and PR-PCSS score at about 12 months post-treatment. Further, such patients have a ≥2-point or ≥1-point improvement from baseline for both the CR-PCSS and PR-PCSS score at about 22 days, 43 days, 90 days, or 180 days after treatment.

In some embodiments, the patients exhibit a ≥3-point improvement from baseline for both the CR-PCSS and PR-PCSS score at about 6 months post-treatment, or have a ≥3-point improvement from baseline for both the CR-PCSS and PR-PCSS score at about 12 months after treatment, or have a ≥3-point improvement from baseline for both the CR-PCSS and PR-PCSS score at about 12 months post-treatment. Further, such patients have a ≥3-point improvement from baseline for both the CR-PCSS and PR-PCSS score at about 22 days, 43 days, 90 days, or 180 days after treatment. In another aspect, the collagenase treatment exhibits durability (as defined herein).

Additional embodiments of the present scales, methods and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIGS. 2A to 2E are a series of photographs depicting the PR-PCSS for the thigh.

FIGS. 3A to 3E are a series of photographs depicting the CR-PCSS for the thigh.

FIGS. 4A to 4E are a series of photographs depicting the PR-PCSS for the buttock.

FIGS. 5A to 5E are a series of photographs depicting the CR-PCSS for the buttock.

DETAILED DESCRIPTION OF THE SPECIFIC EMBODIMENTS

Figure 1:
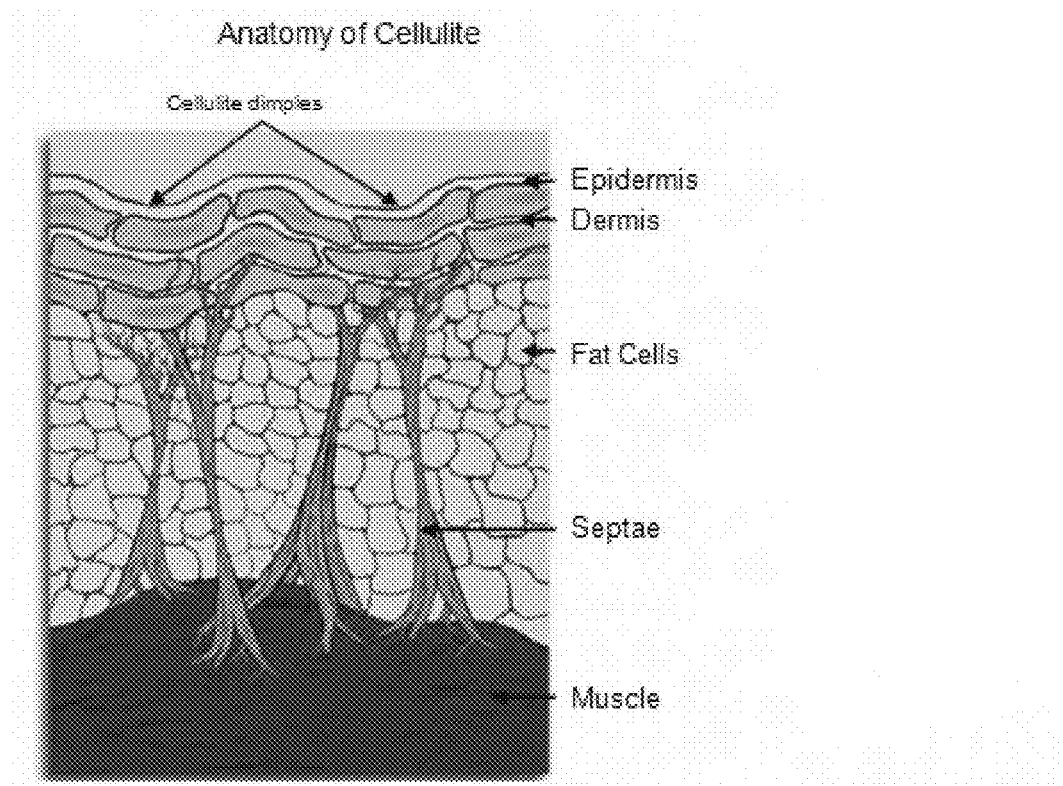
FIG. 1 is illustration of the anatomy of cellulite.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

"Affected area" as used herein means a quadrant (defined below) or other area of cellulite that is to be treated with CCH or any other therapeutic agent or treatment for cellulite.

"Clinician Reported Photonumeric Cellulite Severity Scale (CR-PCSS)" as used herein is the photonumeric scales shown in FIGS. 3A to 3E and 5A to 5E used by physicians/clinicians and designed to quantify the severity of cellulite into 5 levels.

"Composite responders" as used herein means patients that had an improvement of at least 2 levels of cellulite severity in both the PR-PCSS and CR-PCSS.

"Durability" as used herein means 1) the visit date that a subject became a 2-level composite responder until the first date of 2 sequential visits at which the assessment ratings return and are sustained to baseline ratings; and 2) the visit date that a subject became a 1-level composite responder until the first date of 2 sequential visits at which the assessment ratings return and are sustained at baseline ratings.

"Images" as used herein means photographs, illustrations, drawings, models, 3D models, computer-generated images, MRI images and the like.

"Optional" or "optionally" means that the subsequently described element, component or circumstance may or may not occur, so that the description includes instances where the element, component, or circumstance occurs and instances where it does not.

"Patient Reported Photonumeric Cellulite Severity Scale (PR-PCSS)" as used herein is the photonumeric scales shown in FIGS. 2A to 2E and 4A to 4E designed to quantify the severity of cellulite into 5 levels.

"Photonumeric" as used herein means using a series of photographs, illustrations, drawings, models, 3D models, computer-generated images, MRI images, images and the like each assigned a different level of cellulite severity in a scale.

"Quadrant" as used herein means the left buttock, right buttock, left posterolateral thigh, or right posterolateral thigh of the patient.

The terms "subject" or "patient" is used interchangeably herein and refers to a human or other mammal.

The term "therapeutically effective amount," as used herein, refers to the amount of the biologically active agent needed to stimulate or initiate the desired beneficial result. The amount of the biologically active agent employed will be that amount necessary to deliver an amount of the biologically active agent needed to achieve the desired result. In practice, this will vary widely depending upon the particular biologically active agent being delivered, the site of delivery, and the dissolution and release kinetics for delivery of the biologically active agent into skin of the affected area.

The term "treatment session" as used herein means one or more injections or treatments to affected area(s) with a therapeutically effective amount of at least one active agent useful in treating cellulite in a single office visit.

The terms "validated," "validity" or "validation" as used herein mean a process by which a particular scale is demonstrated to be accurate and reliable, including the repeatability of visual assessments to ensure that the same result can be consistently obtained. Validation further examines the precision, accuracy and sensitivity of the scale to confirm the measurements taken by it are reliable, reproducible and robust.

The inventions of the present disclosure satisfy the need for reliable and consistent scales to effectively rate cellulite and, in particular, be used in the treatment thereof. Such scales are important to clinicians and patients to gauge treatment effectiveness. As such, objective quantifications are critical to measure the efficacy of a therapy by comparing the severity of cellulite before and after treatment.

THERAPEUTIC AGENTS

The present disclosure relates to the administration of collagenase obtained or derived (e.g., recombinantly) from *Clostridium histolyticum*. The scales of the present disclosure are used in combination with therapeutic agents to treat and evaluate cellulite. In one embodiment, there is a method for the treatment or alleviation of cellulite in a patient in need thereof, comprising: (a) assessing the severity of the patient's cellulite by using one or more validated photonumeric scales to establish a baseline; (b) injecting a pharmaceutical composition comprising isolated and purified collagenase I and collagenase II in an approximate 1:1 ratio each having a purity of at least 95%, in an amount of about 0.01 mg to about 5 mg (based on the collagenase I/II component) to an affected area where cellulite is present; and (b) evaluating the improvement resulting from such injection by using the one or more validated photonumeric scales.

In one aspect, the collagenase I and II mixture described above may be injected in an amount of about 0.01 mg to 5 mg per treatment session in one or more injections, e.g., the dose is divided equally into about 3 to about 20 injections. The dose of the mixture may comprise about 0.1 mg to 1 mg, or 0.25 mg to 0.75 mg, or 0.1 mg to 2 mg, or 0.25 mg to 1.75 mg, or 0.5 mg to 1 mg, 0.1 mg to 3 mg, or 0.25 mg to 2.75 mg, or 0.5 mg to 2.5 mg, or 0.75 mg to 2.25 mg, or 1 mg to 2 mg, or 0.1 mg to 4 mg, or 0.25 mg to 3.75 mg, or 0.5 mg to 3.5 mg, or 0.75 mg to 3 mg, or 1 mg to 3 mg, or about 0.05 mg, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.25 mg, 2.5 mg, 2.75 mg, 3 mg, 3.25 mg, 3.5 mg, 3.75 mg, 4.0 mg, 4.25 mg, 4.5 mg, 4.75 mg, or 5 mg in one or more injections. In another embodiment, the dose administered is about 0.06 mg, 0.48 mg, 0.84 mg, or 1.68 mg in one or more injections.

For instance, about 0.06 mg, 0.48 mg, 0.84 mg, or 1.68 mg is administered in 12 injections.

The doses of the above-mentioned collagenase mixture can also be expressed in mg per injection such as from about 0.001 mg to 0.5 mg per injection, about 0.01 mg to about 5 mg per injection, or about 0.005 mg to about 0.1 mg, or about 0.005 mg, 0.04 mg, or 0.07 mg per injection. The collagenase mixture may be in the form of a pharmaceutical formulation comprising the collagenase and pharmaceutically acceptable excipients.

Figure 7:
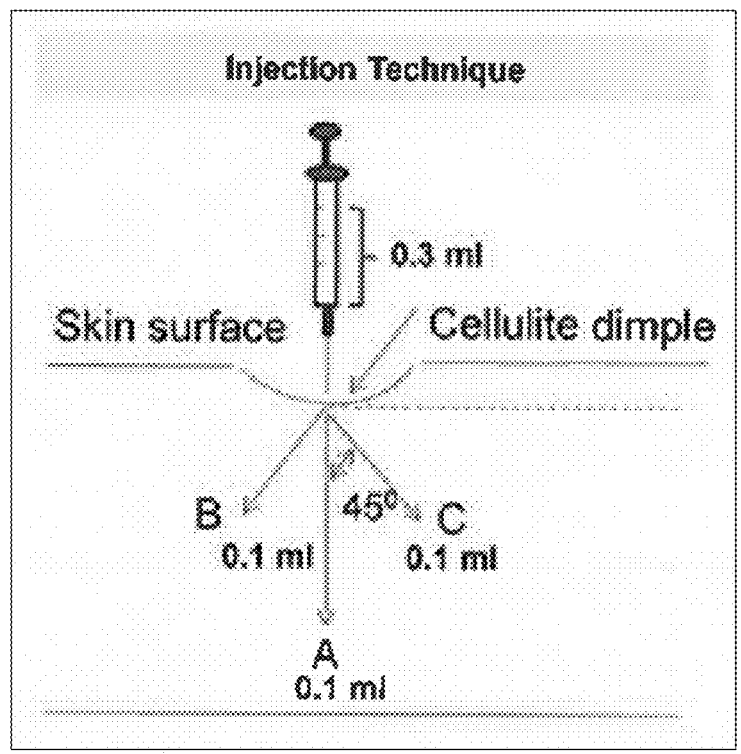
FIG. 7 is an illustration of an injection technique useful in administering CCH or placebo to a cellulite dimple.

For example, about 0.84 mg of the above-mentioned collagenase mixture may be administered in 12 equally divided injections to an affected area every 15-25 days totaling a dose of about 0.84 mg per treatment session (i.e., 0.07 mg×12 injections=0.84 mg). FIG. 7 is one example of an injection technique useful in administering the collagenase mixture to a cellulite dimple. In one embodiment, XIAFLEX® may be employed as the collagenase formulation. Other collagenases that may be suitable are described in U.S. Pat. Nos. 7,811,560; 9,757,435; 9,744,138; and WO2012/125948.

More particularly, various collagenase compositions may be employed having a specific activity of about 10,000 ABC units/mg to about 25,000 ABC units/mg, or about 15,000 ABC units/mg, or about 17,500 ABC units/mg, or about 20,000 ABC units/mg, or about 22,500 ABC units/mg, or about 10,000 ABC units/0.58 mg, or 17,241 ABC units/mg wherein "mg" refers to the amount of collagenase(s) present in a composition (as distinct from excipients and other constituents). Accordingly, the present invention contemplates injecting about 500 ABC units to about 50,000 ABC units per treatment session, or about 10,000 ABC units to about 25,000 ABC units per treatment session.

In another embodiment, the dose of collagenase per injection is about 50 ABC units to about 2,500 ABC units, or about 85 ABC units to about 2,000 ABC units, or about 150 ABC units to about 1,750 ABC units, or about 200 ABC units to about 1,500 ABC units, or about 300 ABC units to about 1,250 ABC units, or about 500 ABC units to about 1,000 ABC units.

While it is preferred that a collagenase I and II mixture be used in an approximate ratio of 1:1, other ratios may be employed such as 0.1-2:1, or 0.25-2:1, or 0.5-2:1, or 0.75-2:1, or 1:0.1-2, or 1:0.25-2, or 1:0.5-2, or 1:0.75-2. Each of collagenase I and II may have a purity by area of at least 80%, or 85%, or 90%, or 91%, or 92%, or 93%, or 94%, or 95%, or 96%, or 97%, or 98%, or 99%, or 100% as measured by reverse phase HPLC.

The volume of collagenase composition injected may range from 0.01 mL to 3 mL per injection, or total about 0.2 mL to 15 mL per treatment session.

The present disclosure is not limited to collagenase as the effectiveness of any therapeutic agent or treatment for cellulite may be measured by the scales disclosed herein.

SCALES

1. Description of Scales

The present disclosure is directed to validated scales to visually characterize the nature, extent and severity of cellulite in human patients. The scales may comprise about 3 to 15 photographs, illustrations, drawings, 3D models, computer images, MRI images and the like wherein they are categorized by level of cellulite severity. The scales may be patient-reported or physician-reported. The levels compare one quadrant (left buttock, right buttock, left posterolateral thigh, or right posterolateral thigh) of the patient to the pictures, labels, and descriptors of the scale and match the patient's cellulite condition to one of the levels of severity of the scale. In one embodiment, the scale has 5 levels, 6 levels, 7 levels, or 8 levels.

In one aspect, Applicant found, inter alia, that its validated 5-point photonumeric scales (CR-PCSS and PR-PCSS) were more reliable, repeatable and subject to less error than known scales. These scales provided upwards of about 40% or 50% or 60% or 70% or 80% consistency across a number of evaluators applying the scale to the same patients. Such intra- and inter-rater reliability is significantly improved as compared to the prior known scales.

The scales disclosed herein identify various characteristics of cellulite selected from the group consisting of the location of dimples, their size, width, diameter, and number, their depth, shape and their distribution (space between dimples). In certain embodiments, the characteristic is that a dimple is at least 1 cm deep but not greater than 2 cm along the long axis.

Besides the CR-PCSS and PR-PCSS, which are detailed in the sections that follow, several other scales may be used in the present disclosure. For example, these include the Hexsel Cellulite Severity Scale (CSS), which consists of five clinical morphologic features of cellulite, as shown in Table 1.

TABLE 1

| | Cellulite Severity Scale (CSS) | |
|---|---|---|
| A | Number of evident depressions | 0 = no depressions |
| | | 1 = small amount: 1-4 depressions are visible |
| | | 2 = Moderate amount: 5-9 depressions |
| | | 3 = large amount: 10 or more depressions |
| B | Depth of depressions | 0 = no depressions |
| | | 1 = superficial depressions |
| | | 2 = medium depth depressions |
| | | 3 = deep depressions |
| C | Morphological appearance of skin surface alterations | 0 = no raised areas |
| | | 1 = orange peel appearance |
| | | 2 = cottage cheese appearance |
| | | 3 = mattress appearance |
| D | Grade of laxity, flaccidity, or sagging skin | 0 = absence of laxity, flaccidity, or sagging skin |
| | | 1 = slight draped appearance |
| | | 2 = moderate draped appearance |
| | | 3 = severe draped appearance |

TABLE 1-continued

Cellulite Severity Scale (CSS)

| | | |
|---|---|---|
| E | Classification scale by Nürnberger and Müller[a] | Stage 0 = No dimpling when the subject is standing and lying. The pinch test reveals "folds and furrows", but there is no mattress-like appearance.<br>Stage 1 = No dimpling while the subject is standing or lying, but the pinch test reveals the mattress-like appearance.<br>Stage 2 = Dimpling appears spontaneously when standing and not lying down.<br>Stage 3 = Dimpling is spontaneously positive standing and lying down. |

Hexsel et al., 2009
[a]Subjects were evaluated in the standing position with relaxed gluteus muscles. However, if the subject had no evident depressions, they were asked to contract their gluteus muscles or the pinch test was applied (by pinching the skin between the thumb and index finger) in order to differentiate between Scores/Grades of zero or 1.

2. CR-PCSS

The Clinician Reported Photonumeric Cellulite Severity Scale (CR-PCSS) refers to the photonumeric scales shown in FIGS. 3A to 3E and 5A to 5E used by physicians/clinicians to quantify the severity of cellulite into 5 levels. More particularly, the characteristics of each level in the CR-PCSS are as follows:

a. CR-PCSS Buttock (FIGS. 5A-5E)
  i. CR-PCSS Rating: 0—None
     Skin appears smooth
     No apparent dimples or ridges even upon close inspection
  ii. CR-PCSS Rating: 1—Almost None
     Very few dimples/ridges
     All the dimples are very shallow or superficial
     The dimples/ridges are difficult to notice without looking closely
  iii. CR-PCSS Rating: 2—Mild
     Several noticeable dimples/ridges
     Most of the dimples would be considered not very deep
     Most of the buttock will be smooth skin with the dimples either spread around or concentrated in one certain area.
  iv. CR-PCSS Rating: 3—Moderate
     Many prominent dimples/ridges, most are quite obvious
     Some of the dimples may be considered somewhat deep, but most would be moderately deep; could have several shallow dimples as well
     Dimples/ridges will generally be spread across whole region of buttock
  v. CR-PCSS Rating: 4—Severe
     A lot of highly noticeable dimples/ridges
     Many of the dimples/ridges would be considered quite deep
     Dimples/ridges would be easily apparent on most of buttock; there would be very little or no smooth skin seen
b. CR-PCSS Thigh (FIGS. 3A-3E)
  i. CR-PCSS Rating: 0—None
     Skin appears smooth
     No apparent dimples or ridges even upon close inspection
  ii. CR-PCSS Rating: 1—Almost None
     Very few dimples/undulations
     All the dimples/undulations are very shallow or superficial
     The dimples/undulations are difficult to notice without looking closely
  iii. CR-PCSS Rating: 2—Mild
     Several noticeable dimples/undulations
     Most of the dimples/undulations would be considered not very deep
     Most of the thigh will be smooth skin with the dimples/undulations either spread around or concentrated in one certain area.
  iv. CR-PCSS Rating: 3—Moderate
     Many prominent dimples/undulations, most are quite obvious
     Some of the dimples/undulations would be considered somewhat deep, but most would be moderately deep; could have several shallow undulations as well
     Dimples/undulations will generally be spread across whole region of thigh
  v. CR-PCSS Rating: 4—Severe
     A lot of highly noticeable dimples/undulations
     Many of the dimples/undulations would be considered quite deep
     Dimples/undulations would be easily apparent on most of thigh; there would be very little or no smooth skin seen

3. PR-PCSS

The Patient Reported Photonumeric Cellulite Severity Scale (PR-PCSS) refers to the photonumeric scales shown in FIGS. 2A to 2E and 4A to 4E used by patients to quantify the severity of their cellulite into 5 levels. More particularly, the PR-PCSS is as follows:

a. PR-PCSS Buttock (FIGS. 4A-4E)
  i. PR-PCSS Rating: 0—None
     No evident cellulite
  ii. PR-PCSS Rating 1—Almost None
     A few superficial dimples or ridges
  iii. PR-PCSS Rating: 2—Mild
     Several dimples or ridges of which most are superficial
  iv. PR-PCSS Rating: 3—Moderate
     Many dimples or ridges of which most are somewhat deep
  v. PR-PCSS Rating: 4—Severe
     A lot of dimples or ridges of which many are deep covering most of the skin area
b. PR-PCSS Thigh (FIGS. 2A-2E)
  i. PR-PCSS Rating: 0—None
     No evident cellulite
  ii. PR-PCSS Rating: 1—Almost None
     A few superficial dimples or ridges iii. PR-PCSS Rating: 2—Mild
   Several dimples or ridges of which most are superficial
iv. PR-PCSS Rating: 3—Moderate
   Many dimples or ridges of which most are somewhat deep
v. PR-PCSS Rating: 4—Severe
   A lot of dimples or ridges of which many are deep covering most of the skin area

DEVELOPMENT AND VALIDATION OF CR-PCSS AND PR-PCSS

1. Introduction

The Clinician-Reported Photonumeric Cellulite Severity Scale (CR-PCSS) for Buttock and Thigh was developed for use by clinicians to assess cellulite on the buttocks and posterolateral thighs and the Patient-Reported Photonumeric Cellulite Severity Scale (PR-PCSS) for Buttock and Thigh was developed for use by patients to rate their own cellulite in the same areas (i.e., left buttock, right buttock, left posterolateral thigh, and right posterolateral thigh). To support clinician assessment and patient self-rating of cellulite, the CR-PCSS and PR-PCSS scales use the same five reference pictures of buttocks and posterolateral thighs that differ in level of cellulite severity, specifically varying by the number and depth of the dimples. Each reference picture is labeled with the associated severity level, NONE, ALMOST NONE, MILD, MODERATE, and SEVERE, with an accompanying descriptor. The CR-PCSS scales are presented in FIGS. 3A-E, 5A-E and the PR-PCSS scales are presented in FIGS. 2A-E, 4A-E.

The CR-PCSS instrument content and preliminary support of content validity were established through concept elicitation and cognitive interviews. The goal was to develop a simple assessment tool for investigators that would be static, non-comparative in nature and would include response categories that correspond to clinically meaningful gradations. In a clinical setting, the CR-PCSS will be used prior to treatment to assess initial cellulite severity and then again after completion of treatment to assess cellulite severity post-treatment.

2. Scale Validation

CR-PCSS Validation by Photographs

To evaluate the reliability of the instruments, the CR-PCSS was evaluated in a test-retest study during which five clinicians rated a total of 200 photographic images, representing levels of cellulite severity ranging from none to severe, from 164 subjects available from three different sources. Half of the photographic images were of the buttock region and half of the thigh region. Intra- and inter-rater reliability of the scale were evaluated through assessments conducted over two time points approximately two weeks apart. Intra-rater reliability assesses an individual clinician's or patient's ratings. Inter-rater reliability assesses ratings assigned by a group of clinicians or patients.

The CR-PCSS demonstrated good reliability with intra-rater reliability for the buttock scale ranging from 0.80 to 0.89 for ICC (C, 1) and ICC (A, 1) (McGraw & Wong 1996) and for the thigh scale ranging from 0.75 to 0.86 for ICC (C, 1) and ICC (A, 1) (McGraw & Wong 1996). Most of the lower bounds of the 95% confidence intervals (CI) were all above 0.75. ICC(C,1) refers to consistency across assessments, and ICC(A,1) refers to absolute agreement among the assessments.

The intra-rater reliability was calculated for each rater using ICC (C,1) and ICC (A,1). All ICC(C,1) and ICC(A,1) point estimates exceeded 0.80. Most ICC(C,1) and ICC(A,1) confidence interval lower limits for the clinicians' ratings of the buttock images were greater than 0.70. The exception was clinician 4 for ICC(A,1), whose lower limit was 0.632. ICC(C,1) ranged from 0.840 (0.771, 0.889) to 0.903 (0.860, 0.934) and ICC(A,1) ranged from 0.804 (0.632, 0.887) to 0.894 (0.833, 0.931) [Table 2]. Clinician agreement percentages between assessments ranged from 53% for clinician 4 to 76% for clinician 5.

TABLE 2

Buttock: Intra-Rater Reliabilities for Clinicians (N = 100 Images)

| Clinician ID | ICC(C, 1) | ICC(A, 1) | Agreement Percentages |
|---|---|---|---|
| Clinician 1 | 0.903 (0.860, 0.934) | 0.894 (0.833, 0.931) | 73 (73.0%) |
| Clinician 2 | 0.885 (0.835, 0.921) | 0.868 (0.772, 0.919) | 73 (73.0%) |
| Clinician 3 | 0.881 (0.828, 0.918) | 0.882 (0.829, 0.919) | 70 (70.0%) |
| Clinician 4 | 0.840 (0.771, 0.889) | 0.804 (0.632, 0.887) | 53 (53.0%) |
| Clinician 5 | 0.896 (0.850, 0.929) | 0.886 (0.822, 0.926) | 76 (76.0%) |

Abbreviations:
ID = Identification;
CI = Confidence Interval;
ICC = Intraclass correlation;
SD = Standard Deviation All ICC(C,1) and ICC(A,1) point estimates exceeded 0.70, with several exceeding 0.80. In 3 of 5 cases, the ICC(C,1) confidence limit lower limits for the clinicians rating the thigh images were greater than 0.70. ICC(C,1) ranged from 0.766 (0.672, 0.836) to 0.859 (0.797, 0.903) and ICC(A,1) ranged from 0.750 (0.412, 0.875) to 0.860 (0.799, 0.904) [Table 3]. Clinician agreement percentages between assessments ranged from 53% for clinician 4 to 75% for clinician 1.

TABLE 3

Thigh: Intra-Rater Reliabilities for Clinicians (N = 100 Images)

| Clinician ID | ICC(C, 1) | ICC(A, 1) | Agreement Percentages |
|---|---|---|---|
| Clinician 1 | 0.859 (0.797, 0.903) | 0.860 (0.799, 0.904) | 75 (75.0%) |
| Clinician 2 | 0.766 (0.672, 0.836) | 0.752 (0.642, 0.830) | 61 (61.0%) |
| Clinician 3 | 0.781 (0.692, 0.847) | 0.780 (0.690, 0.847) | 69 (69.0%) |
| Clinician 4 | 0.820 (0.744, 0.875) | 0.750 (0.412, 0.875) | 53 (53.0%) |
| Clinician 5 | 0.803 (0.720, 0.863) | 0.769 (0.608, 0.859) | 64 (64.0%) |

Abbreviations:
ID = Identification;
CI = Confidence Interval;
ICC = Intraclass correlation;
SD = Standard Deviation The inter-rater reliability was calculated between raters at Assessment 1 and Assessment 2 using ICC(C,1: degree of consistency across assessments) and ICC(A,1: degree of absolute agreement among the assessments). At Assessment 1 (Table 4), the between-clinician rating agreement percentages for the buttock images ranged from 53% (clinician 2 and clinician 4) to 72% (clinician 3 and clinician 5). At Assessment 2 (Table 5), the between-clinician rating agreement percentages ranged from 56% (clinician 2 and clinician 4) to 73% (clinician 3 and clinician 5).

TABLE 4

Buttock: Between-clinician Rating Agreement Percentages, Assessment 1 (N = 100)

| Clinician ID | Clinician 1 | Clinician 2 | Clinician 3 | Clinician 4 | Clinician 5 |
|---|---|---|---|---|---|
| Clinician 1 | — | | | | |
| Clinician 2 | 62 (62.0%) | — | | | |
| Clinician 3 | 68 (68.0%) | 63 (63.0%) | — | | |
| Clinician 4 | 68 (68.0%) | 53 (53.0%) | 61 (61.0%) | — | |
| Clinician 5 | 70 (70.0%) | 61 (61.0%) | 72 (72.0%) | 60 (60.0%) | — |

Abbreviations:
ID = Identification

TABLE 5

Buttock: Between-clinician Rating Agreement Percentages, Assessment 2 (N = 100)

| Clinician ID | Clinician 1 | Clinician 2 | Clinician 3 | Clinician 4 | Clinician 5 |
|---|---|---|---|---|---|
| Clinician 1 | — | | | | |
| Clinician 2 | 61 (61.0%) | — | | | |
| Clinician 3 | 69 (69.0%) | 57 (57.0%) | — | | |
| Clinician 4 | 69 (69.0%) | 56 (56.0%) | 72 (72.0%) | — | |
| Clinician 5 | 68 (68.0%) | 58 (58.0%) | 73 (73.0%) | 69 (69.0%) | — |

Abbreviations:
ID = Identification

The ICC confidence interval lower limits at Assessment 1 and Assessment 2 were greater than 0.70. At Assessment 1, the ICC(C,1) was 0.856 (0.813, 0.892) and the ICC(A,1) was 0.839 (0.785, 0.883). At Assessment 2, the ICC(C,1) was 0.845 (0.799, 0.884) and the ICC(A,1) was 0.834 (0.782, 0.877) [Table 6].

TABLE 6

Buttock: Inter-Rater Reliability, Assessment 1 and Assessment 2 (N = 100)

| Assessment | ICC(C, 1) | ICC(A, 1) |
|---|---|---|
| Assessment 1 | 0.856 (0.813, 0.892) | 0.839 (0.785, 0.883) |
| Assessment 2 | 0.845 (0.799, 0.884) | 0.834 (0.782, 0.877) |

Abbreviations:
CI = Confidence Interval;
ICC = Intraclass correlation

At Assessment 1, the between-clinician rating agreement percentages for the thigh images ranged from 39% (clinician 2 and clinician 4) to 65% (clinician 1 and clinician 5) [Table 7]. At Assessment 2, the between-clinician rating agreement percentages ranged from 39% (clinician 2 and clinician 4) to 70% (clinician 1 and clinician 5) [Table 8].

TABLE 7

Between-clinician Rating Agreement Percentages, Assessment 1 (N = 100)

| Clinician ID | Clinician 1 | Clinician 2 | Clinician 3 | Clinician 4 | Clinician 5 |
|---|---|---|---|---|---|
| Clinician 1 | — | | | | |
| Clinician 2 | 62 (62.0%) | — | | | |
| Clinician 3 | 60 (60.0%) | 57 (57.0%) | — | | |
| Clinician 4 | 48 (48.0%) | 39 (39.0%) | 55 (55.0%) | — | |
| Clinician 5 | 65 (65.0%) | 48 (48.0%) | 63 (63.0%) | 64 (64.0%) | — |

Abbreviations:
ID = Identification

TABLE 8

Thigh: Between-clinician Rating Agreement Percentages, Assessment 2 (N = 100)

| Clinician ID | Clinician 1 | Clinician 2 | Clinician 3 | Clinician 4 | Clinician 5 |
|---|---|---|---|---|---|
| Clinician 1 | — | | | | |
| Clinician 2 | 48 (48.0%) | — | | | |
| Clinician 3 | 69 (69.0%) | 39 (39.0%) | — | | |
| Clinician 4 | 61 (61.0%) | 54 (54.0%) | 65 (65.0%) | — | |
| Clinician 5 | 70 (70.0%) | 47 (47.0%) | 69 (69.0%) | 58 (58.0%) | — |

Abbreviations:
ID = Identification

The ICC confidence interval lower limits at Assessment 1 and Assessment 2 were greater than 0.70. At Assessment 1, the ICC(C,1) was 0.765 (0.702, 0.821) and the ICC(A,1) was 0.718 (0.616, 0.798). At Assessment 2, the ICC(C,1) was 0.766 (0.704, 0.822) and the ICC(A,1) was 0.731 (0.643, 0.803) [Table 9].

TABLE 9

Thigh: Inter-Rater Reliability, Assessment 1 and Assessment 2 (N = 100)

| Assessment | ICC(C, 1) | ICC(A, 1) |
| --- | --- | --- |
| Assessment 1 | 0.765 (0.702, 0.821) | 0.718 (0.616, 0.798) |
| Assessment 2 | 0.766 (0.704, 0.822) | 0.731 (0.643, 0.803) |

Abbreviations:
CI = Confidence Interval;
ICC = Intraclass correlation

Key study highlights include:
  i. Four of 5 clinicians agreed on the ratings for greater than or equal to 70% of 100 images between the 2 assessments of buttock cellulite severity,
  ii. Four of 5 clinicians agreed on the ratings for greater than or equal to 60% of 100 images between the 2 assessments of thigh cellulite severity; and
  iii. The inter-rater reliability agreement percentages for clinician ratings of 100 photographs ranged from about 53% to about 76% for buttock and about 53% to about 75% for thigh.

PR-PCSS Validation by Photographs

The PR-PCSS content validity was assessed through concept elicitation interviews with 26 subjects with cellulite and through cognitive interviews with 23 subjects with cellulite. To evaluate the reliability of the instrument, the test-retest reliability of the PR-PCSS was previously evaluated in a sample of 99 subjects with varying levels of cellulite severity.

Cellulite was assessed separately on the thigh and the buttock regions using the PR-PCSS at two study visits separated by approximately 14 days. Over two time points approximately two weeks apart, subjects self-rated their cellulite severity using high quality photographs taken using Canfield's Vectra® camera. The PR-PCSS demonstrated acceptable reliability for the buttock scale, with the intra-rater estimates for the buttock scale from 0.86 to 0.87 for ICC (C, 1) and ICC (A, 1) and for the thigh scale from 0.83 to 0.86 for ICC (C, 1) and ICC (A, 1) with the lower bounds of the 95% confidence intervals (CI) for all areas above 0.75.

The intra-rater reliability by patients was calculated using ICC(C,1: degree of consistency across assessments) and ICC(A,1: degree of absolute agreement among the assessments) [Table 10]. For the left buttock and the right buttock the ICC(C,1) and ICC(A,1) were the same within each quadrant: left buttock=0.87 (95% CI: 0.813, 0.911), right buttock=0.86 (95% CI: 0.794, 0.901). This similarity of results within quadrant was apparent for the thigh ratings as well: the ICC(C,1) for the left thigh was 0.86 (95% CI: 0.793, 0.901) and the ICC(A,1) was 0.86 (95% CI: 0.795, 0.902). The ICC(C,1) was 0.83 after rounding (95% CI: 0.755, 0.881) for the right thigh and the ICC(A,1) was 0.83 (95% CI: 0.756, 0.882).

TABLE 10

Intra-Rater Reliability for Visit 1 and Visit 2 (n = 99)

| | Intra-Rater Reliability | |
| --- | --- | --- |
| | ICC (C, 1) (95% CI) | ICC (A, 1) (95% CI) |
| Left Buttock | 0.870 (0.813, 0.911) | 0.870 (0.813, 0.911) |
| Right Buttock | 0.856 (0.794, 0.901) | 0.857 (0.794, 0.901) |
| Left Thigh | 0.856 (0.793, 0.901) | 0.858 (0.795, 0.902) |
| Right Thigh | 0.828 (0.755, 0.881) | 0.830 (0.756, 0.882) |

CR-PCSS Live Assessment, Test-Retest Reliability

Applicant further performed a non-interventional study to evaluate intra- and inter-rater reliability of the CR-PCSS in live ("in person") patients as assessed by clinicians, and its concordance with PR-PCSS. More particularly, this study was performed to evaluate (1) the comparability of two methods of self-rating: one using mirrors for live assessment and the other using photographs, and (2) the association between clinician- and self-ratings.

Test-retest reliability of the CR-PCSS was evaluated at baseline and Day 2. To minimize clinician reliance on memory, patient order was changed on Day 2 and clinicians were not permitted visual or vocal cues, or touching of patients. The same patients included in clinician assessment of the CR-PCSS used the PR-PCSS to self-rate cellulite severity, using either photos or mirrors at baseline and the other method 14 days later; method order was randomly assigned. Intra- and inter-rater (CR-PCSS) reliability were estimated using intraclass correlation coefficients for agreement (ICC), and corresponding 95% confidence intervals (CI) were calculated. Concordance of the CR-PCSS with PR-PCSS ratings was calculated for the left or right buttock and left or right thigh at baseline.

Six clinicians included as CR-PCSS raters were predominantly male (n=5; 83.3%), had practiced medicine for a mean of 21.3 years (range, 4-54 years), and specialized in plastic surgery (n=3; 50%) or dermatology (n=3; 50%). The 76 patients had a mean age of 45.1 years (range, 18-71 years) and were mostly White (n=53; 69.7%); the majority self-identified as having cellulite on both thighs and buttocks (n=58; 76.3%). The overall mean (95% CI) ICC point estimates for clinician intra-rater reliability of the CR-PCSS between baseline and Day 2 for both the left and right buttock were 0.81 (0.73, 0.90) and 0.81 (0.72, 0.90), and for the left and right thigh were 0.78 (0.67, 0.90) and 0.79 (0.67, 0.90), indicating reliability of ICCs across quadrants. At baseline, overall mean (95% CI) ICC point estimates for clinician inter-rater reliability for the left and right buttock were 0.76 (0.69, 0.83) and 0.76 (0.68, 0.82), and for the left and right thigh were 0.74 (0.67, 0.81) and 0.75 (0.68, 0.82). Intra- and inter-rater reliability for the CR-PCSS were considered within the acceptable range for all areas, with 95% CI lower-bound estimates near or above 0.70, and upper-bound estimates at approximately 0.90. At baseline, concordance (ICC [95% CI]) between the CR-PCSS and PR-PCSS (across methods) for the left and right buttock were 0.51 (0.32, 0.66) and 0.56 (0.38, 0.70), and for the left and right thigh were 0.61 (0.44, 0.73) and 0.67 (0.53, 0.78).

Intra-rater reliability was evaluated through both descriptive tables comparing scores at the two assessment points and through the use of ICCs. The descriptive analyses found that for buttock ratings, clinicians agreed with themselves 49%-79% of the time across the two visits, and were within one level of perfect agreement between 89% and 92% of the time. For thigh ratings, the rates of perfect agreement were 41%-82% of the time, with agreement within one level 93%-94% of the time. These high rates of variability in within-clinician concordance are noteworthy, and in every instance, either Clinician 6 (protocol deviation described above) or Clinician 3 had the lowest rates of self-agreement. The mean intra-rater ICCs were within the acceptable range and consistent across both buttock areas (left buttock ICC (A,1) 0.81, 95% CI 0.725 to 0.901; right buttock ICC(A,1) 0.81, 95% CI 0.718 to 0.897). For the thigh areas, the mean ICCs were acceptable and similar across both thigh areas (left thigh ICC(A,1) 0.78, 95% CI 0.670 to 0.899; right thigh ICC(A,1) 0.79, 95% CI 0.671 to 0.901).

Overall, intra-rater reliability as calculated by ICCs was within the acceptable range for all areas with 95% confidence interval lower bound estimates near or above 0.70 and upper bound estimates at approximately 0.90. Relative to the thigh areas, the buttock areas were observed to have higher levels of intra-rater reliability based on numerical values of the ICCs.

TABLE 11

Overall Mean Intra-Rater Reliabilities for Clinicians by Area

| Area | Intra-Rater Reliability Overall Mean ICC (SD) [95% CI] | |
|---|---|---|
| | ICC (C, 1), (95% CI) | ICC (A, 1), (95% CI) |
| Left Buttock | 0.83(.07, ), [0.747, 0.904] | 0.81(0.08), [0.725, 0.901] |
| Right Buttock | 0.82(0.07), [0.743, 0.900] | 0.81(0.09), [0.718, 0.897] |
| Left Thigh | 0.80(0.09), [0.709, 0.891] | 0.78(0.11), [0.670, 0.899] |
| Right Thigh | 0.80(0.10), [0.699, 0.901] | 0.79(0.11), [0.671, 0.901] |

The mean intra-rater ICCs were within the acceptable range and consistent across both buttock areas (left buttock ICC(A,1) 0.81, 95% CI 0.725 to 0.901; right buttock ICC (A,1) 0.81, 95% CI 0.718 to 0.897). For the thigh areas, the mean ICCs were acceptable and similar across both thigh areas (left thigh ICC(A,1) 0.78, 95% CI 0.670 to 0.899; right thigh ICC(A,1) 0.79, 95% CI 0.671 to 0.901).

Overall, intra-rater reliability as calculated by ICCs was within the acceptable range for all areas with 95% confidence interval lower bound estimates near or above 0.70 and upper bound estimates at approximately 0.90. Relative to the thigh areas, the buttock areas were observed to have higher levels of intra-rater reliability based on numerical values of the ICCs.

Inter-rater reliability was likewise evaluated in a descriptive manner (Section 3.1.3) as well as using ICCs. Rates of agreement across buttock ratings were such that at least four clinicians agreed on 68%-74% of ratings across areas (left and right) and visits. For thighs, at least four clinicians agreed from 71%-82% of the time across areas and visits. Slightly higher levels of inter-rater agreement were observed at Baseline when compared with Day 2.

Across both buttock areas, Baseline inter-rater reliabilities as evaluated by ICCs were observed in the acceptable range at 0.76 (left buttock ICC(A,1) 0.76, 95% CI 0.691 to 0.827; right buttock ICC(A,1) 0.76, 95% CI 0.68 to 0.823) and at approximately 0.70 at Day 2 (left buttock ICC(A,1) 0.71, 95% CI 0.577 to 0.805; right buttock ICC(A,1) 0.70, 95% CI 0.56 to 0.795). For both thigh areas, Baseline inter-rater reliabilities as evaluated by ICCs were observed in the acceptable range at 0.74 and 0.75 (left thigh ICC(A,1) 0.74, 95% CI 0.67 to 0.811; right thigh ICC(A,1) 0.75, 95% CI 0.677 to 0.817) and at approximately 0.70 at Day 2 (left thigh ICC(A,1) 0.699, 95% CI 0.562 to 0.798; right thigh ICC(A,1) 0.704, 95% CI 0.566 to 0.803). Overall, inter-rater reliability as calculated by ICCs was within the acceptable range for all areas.

Concordance of CR-PCSS and PR-PCSS

Inter-Rater Reliability Between Clinicians and Subjects via Photos—Left Buttock—The inter-rater reliabilities between the CR- and PR-PCSS was calculated between all the six clinicians and the subject ratings were calculated using ICC(C,1) and ICC(A,1). ICC values were generated for each methodology of subject ratings on the PR-PCSS using either photographs or minors. Clinician ratings were randomly selected and subject photo ratings were pooled from Baseline and Day 14+3 of assessment for each subject. In the following tables, "Random Clinician A" and "Random Clinician B are randomly selected clinicians to match with each subject. Each order is different.

TABLE 12

Left Buttock: Inter-rater Reliability Between CR-PCSS and PR-PCSS (Photo) (N = 75)

| | Inter-Rater Reliability | |
|---|---|---|
| | ICC (C, 1) (95% CI) | ICC (A, 1) (95% CI) |
| Random Clinician A | 0.486 (0.293, 0.641) | 0.480 (0.250, 0.623) |
| Random Clinician B | 0.641 (0.487, 0.757) | 0.629 (0.467, 0.749) |

Note.
For this analysis, the clinician rating was randomly selected from among the 6 clinicians separately for each subject (Random Clinician A). For Random Clinician B, the random selection process was repeated.
The subject ratings are based on the PR-PCSS self-ratings using photographs from Baseline and Day 14 period.

The inter-rater reliability between two randomly selected clinician ratings and combined subject ratings from photographic images (N=75) of their cellulite was compared. For Random Clinician A the ICC(C,1) was 0.486 (0.293,0.641) and the ICC(A,1) was 0.460 (0.256,0.623). For Random Clinician B, the ICC(C,1) was 0.641 (0.487,0.757) and the ICC(A,1) was 0.629 (0.467,0.749) [Table 12].

TABLE 13

Left Buttock: CR-PCSS and PR-PCSS Agreement (Mirror) (N = 75)

| | Inter-Rater Reliability | |
|---|---|---|
| | ICC (C, 1) (95% CI) | ICC (A, 1) (95% CI) |
| Random Clinician A | 0.507 (0.319, 0.657) | 0.504 (0.615, 0.654) |
| Random Clinician B | 0.634 (0.478, 0.752) | 0.637 (0.48, 0.754) |

Note.
For this analysis, the clinician rating was randomly selected from among the 6 clinicians, separately for each subject (Random Clinician A). For Random Clinician B, the random selection process was repeated.
The subject ratings are based on the PR-PCSS self-ratings using photographs from Baseline and Day 24 pooled.

The inter-rater reliability between two randomly selected clinician ratings and subject ratings from mirror images (N=75) of their cellulite was compared. For Random Clinician A, the ICC(C,1) was 0.507 (0.319,0.657) and the ICC(A,1) was 0.504 (0.316,0.654). For Random Clinician B, the ICC(C,1) was 0.504 (0.316,0.654) and the ICC(A,1) was 0.637 (0.48,0.754) subject [Table 13].

TABLE 14

Right Buttock: CR-PCSS and PR-PCSS Agreement (Photo) (N = 75)

| | Inter-Rater Reliability | |
|---|---|---|
| | ICC (C, 1) (95% CI) | ICC (A, 1) (95% CI) |
| Random Clinician A | 0.468 (0.272, 0.627) | 0.439 (0.231, 0.608) |
| Random Clinician B | 0.524 (0.339, 0.67) | 0.498 (0.299, 0.654) |

Note.
For this analysis, the clinician rating was randomly selected from among the 6 clinicians, separately for each subject (Clinician 1). For Clinician the random selection process was repeated.
The subject ratings are based on the PR-PCSS self-ratings photographs from Baseline and Day 14 pooled The inter-rater reliability between two randomly selected clinician ratings and subject ratings from photographic images (N=75) of their cellulite was compared. For Random Clinician A ratings, the ICC(C,1) was 0.468 (0.272,0.627) and the ICC(A,1) was 0.439 (0.231,0.608). For Random Clinician B ratings, the ICC(C,1) was 0.524 (0.339,0.67) and the ICC(A,1) was 0.498 (0.299,0.654) subject [Table 14].

TABLE 15

Right Buttock: CR-PCSS and PR-PCSS Agreement (Mirror) (N = 75)

| | Inter-Rater Reliability | |
|---|---|---|
| | ICC(C, 1) (95% CI) | ICC (A, 1) (95% CI) |
| Random Clinician A | 0.606 (0.441, 0.731) | 0.601 (0.435, 0.727) |
| Random Clinician B | 0.679 (0.536, 0.784) | 0.677 (0.533, 0.783) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using mirrors from Baseline and Day 14 pooled The inter-rater reliability between two randomly selected clinician ratings and subject ratings from mirror images (N=75) of their cellulite was compared. For Random Clinician A, the ICC(C,1) was 0.606 (0.441,0.731) and the ICC(A,1) was 0.601 (0.435,0.727). For Random Clinician B, the ICC(C,1) was 0.679 (0.536,0.784) and the ICC(A,1) was 0.677 (0.533,0.783) [Table 15].

TABLE 16

Left Thigh: CR-PCSS and PR-PCSS Agreement (Photo) (N = 75)

| | Inter-Rater Reliability | |
|---|---|---|
| | ICC(C, 1) (95% CI) | ICC (A, 1) (95% CI) |
| Random Clinician A | 0.582 (0.41, 0.713) | |
| Random Clinician B | 0.664 (0.516, 0.773) | 0.543 (0.116, 0.757) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using mirrors from Baseline and Day 14 pooled The inter-rater reliability between two randomly selected clinician ratings and subject ratings from photographic images (N=75) of their cellulite was compared. For Random Clinician A, the ICC(C,1) was 0.582 (0.41,0.713) and the ICC(A,1) was 0.518 (0.253,0.694). For Random Clinician B, the ICC(C,1) was 0.664 (0.516,0.773) and the ICC(A,1) was 0.543 (0.116,0.757) subject [Table 16].

TABLE 17

Left Thigh: CR-PCSS and PR-PCSS Agreement (Mirror) (N = 75)

| | Inter-Rater Reliability | |
|---|---|---|
| | ICC (C, 1) (95% CI) | ICC (A, 1) (95% CI) |
| Random Clinician A | 0.599 (0.432, 0.726) | 0.599 (0.432, 0.726) |
| Random Clinician B | 0.617 (0.456, 0.74) | 0.620 (0.458, 0.742) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using mirrors from Baseline and Day 14 pooled.

The inter-rater reliability between two randomly selected clinician ratings and subject ratings from mirror images (N=75) of their cellulite was compared. For Random Clinician A, the ICC(C,1) was 0.599 (0.432,0.726) and the ICC(A,1) was 0.599 (0.432,0.726). For Random Clinician B, the ICC(C,1) was 0.617 (0.456,0.74) and the ICC(A,1) was 0.620 (0.458,0.742) subject [Table 17].

TABLE 18

Right Thigh: CR-PCSS and PR-PCSS Agreement (Photo) (N = 75)

| | Inter-Rater Reliability | |
|---|---|---|
| | ICC (C, 1) (95% CI) | ICC (A, 1) (95% CI) |
| Random Clinician A | 0.640 (0.486, 0.756) | 0.575 (0.300, 0.742) |
| Random Clinician B | 0.690 (0.551, 0.792) | 0.558 (0.093, 0.776) |

Note.
For this analysis, the clinician rating was randomly selected from among the 6 clinicians, separately for each subject (Clinician 1). For Clinician 2, the selection process was repeated.
The subject ratings are based on the PR-PCSS self-ratings using the photographs from Baseline and Day 14 pooled.

The inter-rater reliability between two randomly selected clinician ratings and subject ratings from photographic images (N=75) of their cellulite was compared. For Random Clinician A ratings, the ICC(C,1) was 0.640 (0.486,0.756) and the ICC(A,1) was 0.575 (0.300,0.742). For Random Clinician B ratings, the ICC(C,1) was 0.690 (0.551,0.792) and the ICC(A,1) was 0.558 (0.093,0.776) [Table 18].

TABLE 19

Right Thigh: CR-PCSS and PR-PCSS Agreement (Mirror) (N = 75)

| | Inter-Rater Reliability | |
|---|---|---|
| | ICC (C, 1) (95% CI) | ICC (A, 1) (95% CI) |
| Random Clinician A | 0.615 (0.452, 0.738) | 0.617(0.455, 0.74) |
| Random Clinician B | 0.642 (0.488, 0.758) | 0.639 (0.484, 0.755) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using mirrors from Baseline and Day 14 pooled.

The inter-rater reliability between two randomly selected clinician ratings and subject ratings from mirror images (N-75) of their cellulite was compared. For Random Clinician A, the ICC(C,1) was 0.615 (0.452,0.738) and the ICC(A,1) was 0.617 (0.455,0.74). For Random Clinician B, the ICC(C,1) was 0.642 (0.488,0.758) and the ICC(A,1) was 0.639 (0.484,0.755) [Table 19].

TABLE 20

Left Buttock: CR-PCSS and PR-PCSS Agreement (Baseline)

| | Inter-Rater Reliability | |
|---|---|---|
| | ICC (C, 1) (95% CI) | ICC (A, 1) (95% CI) |
| Random Clinician A | 0.515 (0.328, 0.663) | 0.505 (0.317, 0.655) |
| Random Clinician B | 0.668 (0.521, 0.776) | 0.667 (0.521, 0.776) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using photographs and mirrors pooled from the Baseline Visit.

The inter-rater reliability between two randomly selected clinician ratings and subject ratings from a pooled analysis of both methods—mirrors and photos—was compared at Baseline. For Random Clinician A, the ICC(C,1) was 0.515 (0.328,0.663) and the ICC(A,1) was 0.505 (0.317,0.655). For Random Clinician B, the ICC(C,1) was 0.668 (0.521, 0.776) and the ICC(A,1) was 0.667 (0.521,0.776) [Table 20].

TABLE 21

Right Buttock: CR-PCSS and PR-PCSS Agreement (Baseline)

| | Inter-Rater Reliability | |
|---|---|---|
| | ICC (C, 1) (95% CI) | ICC (A, 1) (95% CI) |
| Random Clinician A | 0.563 (0.387, 0.699) | 0.557 (0.381, 0.685) |
| Random Clinician B | 0.592 (0.423, 0.721) | 0.59 (0.421, 0.719) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using photographs and mirrors pooled from the Baseline Visit.

The inter-rater reliability between two randomly selected clinician ratings and subject ratings from a pooled analysis of both methods—mirrors and photos—was compared at Baseline. For Random Clinician A, the ICC(C,1) was 0.563 (0.387,0.699) and the ICC(A,1) was 0.557 (0.381,0.695). For Random Clinician B, the ICC(C,1) was 0.592 (0.423, 0.721) and the ICC(A,1) was 0.59 (0.421,0.719) [Table 21].

TABLE 22

Left Thigh: CR-PCSS and PR-PCSS Agreement (Baseline)

| | Inter-Rater Reliability | |
|---|---|---|
| | ICC (C, 1) (95% CI) | ICC (A, 1) (95% CI) |
| Random Clinician A | 0.609 (0.445, 0.733) | 0.607 (0.443, 0.732) |
| Random Clinician B | 0.615 (0.452, 0.738) | 0.592 (0.413, 0.725) |

Note.
For this analysis, the clinician rating was randomly selected from among the 6 clinicians, separately for each subject (Clinician 1). For Clinician 2, the random selection process was repeated.
The subject ratings are based on the PR-PCSS self-ratings using photographs and mirrors pooled from the Baseline Visit.

The inter-rater reliability between two randomly selected clinician ratings and subject ratings from a pooled analysis of both methods—mirrors and photos—and compared at Baseline. For Random Clinician A, the ICC(C,1) was 0.609 (0.445,0.733) and the ICC(A,1) was 0.607 (0.443,0.732). For Random Clinician B, the ICC(C,1) was 0.615 (0.452, 0.738) and the ICC(A,1) was 0.592 (0.413,0.725) [Table 22].

Across both buttock areas, Baseline inter-rater reliabilities as evaluated by ICCs were observed in the acceptable range at 0.76 (left buttock ICC(A,1) 0.76, 95% CI 0.691 to 0.827; right buttock ICC(A,1) 0.76, 95% CI 0.68 to 0.823) and at approximately 0.70 at Day 2 (left buttock ICC(A,1) 0.71, 95% CI 0.577 to 0.805; right buttock ICC(A,1) 0.70, 95% CI 0.56 to 0.795).

For both thigh areas, Baseline inter-rater reliabilities as evaluated by ICCs were observed in the acceptable range at 0.74 and 0.75 (left thigh ICC(A,1) 0.74, 95% CI 0.67 to 0.811; right thigh ICC(A,1) 0.75, 95% CI 0.677 to 0.817) and at approximately 0.70 at Day 2 (left thigh ICC(A,1) 0.699, 95% CI 0.562 to 0.798; right thigh ICC(A,1) 0.704, 95% CI 0.566 to 0.803). Overall, inter-rater reliability as calculated by ICCs was within the acceptable range for all areas.

The above describes two integrated studies evaluating the CR-PCSS and PR-PCSS. The CR-PCSS study was designed to provide a robust evaluation of the test-retest reliability of the CR-PCSS in using live assessments of cellulite severity in live subjects as all previous validation work on the scale was conducted with photographs. The PR-PCSS study was conducted to evaluate the methods concordance between self-ratings conducted with minor and photographs. Other study objectives were to evaluate the comparability of the CR-PCSS with the PR-PCSS.

These analyses supported the conclusion that the scale demonstrates good reliability for all areas, over time, as an assessment of cellulite severity. The point estimates for intra-rater reliability were nearly all clearly in the acceptable range. The average ICC(A,1) was 0.81 (SD=0.08), ranging from 0.69 to 0.91, and the lower bounds of the confidence intervals ranged from 0.53 to 0.86. The comparable results for the ICC(C,1) were all somewhat higher.

The results for the PR-PCSS were evaluated for their correspondence with the CR-PCSS and for the comparability of mirror vs. photo self-ratings. The results of the ICC analyses indicated that the clinicians tended to agree more with the subjects rating themselves with mirrors rather than photos, with the ICC(A.1) ranging from 0.50 to 0.68 for mirrors, and 0.44 to 0.63 for photos.

PR-PCSS Method Comparison

The PR-PCSS method comparability was calculated between the subjects per area by alternating the day of photo and minor assessment. This was calculated using ICC(C,1: degree of consistency across assessments) and ICC(A,1: degree of absolute agreement among the assessments). The intra-rater reliability for each area in subjects who self-evaluated using mirrors at Baseline and photos at Day 14+3 was evaluated. Seven out of eight point estimates were >0.7, with the exception of ICC(A,1) for left thigh which was 0.696. The lower bound confidence interval ranged widely from 0.304 to 0.669. The ICC(C,1) ranged from 0.745 (0.556,0.861) for the right buttock to 0.815 (0.669,0.901) for the left buttock. The ICC (A,1) ranged from 0.696 (0.304, 0.860) for the left thigh to 0.811 (0.662,0.899) for the left buttock.

The intra-rater reliability for each area in subjects who self-evaluated using mirrors at Baseline and photos at Day 14+3 was evaluated. All the eight point estimates were <0.7. The lower bound confidence interval ranged widely from 0.068 to 0.495. The ICC(C,1) ranged from 0.601 (0.358, 0.768) for the right thigh to 0.697 (0.495,0.829) for the left buttock. The ICC (A,1) ranged from 0.484 (0.068,0.730) for the right thigh to 0.683 (0.471,0.821) for the left buttock.

The inter-rater reliabilities between the CR- and PR-PCSS was calculated between all the six clinicians and the subject ratings were calculated using ICC(C,1) and ICC(A,1). ICC values were generated for each methodology of subject ratings on the PR-PCSS using either photographs or minors. Clinician ratings were randomly selected and subject photo ratings were pooled from Baseline and Day 14+3 of assessment for each subject. In the following tables, "Random Clinician A" and "Random Clinician B are randomly selected clinicians to match with each subject. Each order is different.

The PR-PCSS Method comparability was calculated between the subjects per area by alternating the day of photo and mirror assessment. This was calculated using ICC(C,1: degree of consistency across assessments) and ICC(A,1: degree of absolute agreement among the assessments).

The intra-rater reliability for each area in subjects who self-evaluated using mirrors at Baseline and photos at Day 14+3 was evaluated. Seven out of eight point estimates were >0.7, with the exception of ICC(A,1) for left thigh which was 0.696. The lower bound confidence interval ranged widely from 0.304 to 0.669. The ICC(C,1) ranged from 0.745 (0.556,0.861) for the right buttock to 0.815 (0.669, 0.901) for the left buttock. The ICC (A,1) ranged from 0.696 (0.304,0.860) for the left thigh to 0.811 (0.662,0.899) for the left buttock.

The intra rater reliability for each area in subjects who self-evaluated using mirrors at Baseline and photos at Day 14+3 was evaluated. All the eight point estimates were <0.7. The lower bound confidence interval ranged widely from 0.068 to 0.495. The ICC(C,1) ranged from 0.601 (0.358, 0.768) for the right thigh to 0.697 (0.495,0.829) for the left buttock. The ICC (A,1) ranged from 0.484 (0.068,0.730) for the right thigh to 0.683 (0.471,0.821) for the left buttock.

In summary, applicant demonstrated the test-retest reliability and inter-rater reliability of the CR-PCSS in live subjects. The CR-PCSS and the PR-PCSS produced acceptably comparable ratings when comparing clinician ratings with subject self-ratings. The CR-PCSS was determined to be a reliable tool for evaluating cellulite severity of the buttocks and thighs and correlates well with the PR-PCSS. Thus, the CR-PCSS and the PR-PCSS are valid and reliable tools for evaluating cellulite severity.

USE OF THE SCALES IN EVALUATION AND TREATMENT

1. Generally

In one embodiment, the present disclosure provides a method for rating the severity of cellulite on a thigh or buttock in a human subject, comprising:
  a. assessing a quadrant of the subject's thigh or buttock surface exhibiting signs of cellulite;
  b. assessing the severity of the subject's cellulite comprising using a validated photonumeric scale or the CR-PCSS or PR-PCSS scale; and
  c. classifying, using images, the severity of the subject's cellulite into at least five classes of increasing severity.

As described herein and shown in FIGS. 3A-3E, there is a method for rating the severity of cellulite on a thigh in a human subject, comprising:
  a. assessing a quadrant of the subject's thigh surface exhibiting signs of cellulite;
  b. assessing the severity of the subject's cellulite comprising using a CR-PCSS scale; and
  c. classifying, using images, the severity of the subject's cellulite into at least five classes of increasing severity, wherein a classification into the lowest class (0) indicates no depressions or raised areas, class 1 indicates a few depressions or undulations that are mostly superficial in depth, class 2 indicates several undulations that are shallow in depth with areas of slight protuberances, class 3 indicates many undulations with alternating areas of protuberances and depressions of which most are moderate in depth, and class 4 indicates a lot of undulations with alternating areas of protuberances and depressions, some of more severe depth.

As described herein and shown in FIGS. 2A-2E, there is a method for rating the severity of cellulite on a thigh in a human subject, comprising:
  a. assessing a quadrant of the subject's thigh surface exhibiting signs of cellulite;
  b. assessing the severity of the subject's cellulite comprising using a PR-PCSS scale; and
  c. classifying, using images, the severity of the subject's cellulite into at least five classes of increasing severity, wherein a classification into the lowest class (0) indicates no evident cellulite, class 1 indicates a few superficial dimples or ridges, class 2 indicates several dimples or ridges of which most are superficial, class 3 indicates many dimples or ridges of which most are somewhat deep, and class 4 indicates a lot of dimples or ridges of which many are deep covering most of the skin area.

As described herein and shown in FIGS. 4A-4E, there is a method for rating the severity of cellulite on a buttock in a human subject, comprising:
  a. assessing a quadrant of the subject's buttock surface exhibiting signs of cellulite;
  b. assessing the severity of the subject's cellulite comprising using a PR-PCSS scale; and
  c. classifying, using images, the severity of the subject's cellulite into at least five classes of increasing severity, wherein a classification into the lowest class (0) indicates no evident cellulite, class 1 indicates a few superficial dimples or ridges, class 2 indicates several dimples or ridges of which most are superficial, class 3 indicates many dimples or ridges of which most are somewhat deep, and class 4 indicates a lot of dimples or ridges of which many are deep covering most of the skin area.

As described herein and shown in FIGS. 5A-5E, there is a method for rating the severity of cellulite on a buttock in a human subject, comprising:
  a. assessing a quadrant of the subject's buttock surface exhibiting signs of cellulite;
  b. assessing the severity of the subject's cellulite comprising using a CR-PCSS scale; and
  c. classifying, using images, the severity of the subject's cellulite into at least five classes of increasing severity, wherein a classification into the lowest class (0) indicates no dimples or evident cellulite, class 1 indicates a few dimples that are mostly superficial in depth, class 2 indicates several dimples of which most are shallow in depth, class 3 indicates many dimples of which most are moderate in depth, and class 4 indicates a lot of dimples with some of more severe depth.

The method optionally includes the use of the PR-PCSS either alone or in combination with the CR-PCSS.

There is also a method of assessing severity of cellulite in a human subject, comprising:

a. Selecting a portion of the subject's thigh or buttock to evaluate;
b. comparing the portion of the thigh or buttock to a series of photographs each with corresponding numbers as described in FIGS. 2 to 5;
c. identifying the photograph closest in appearance to the selected portion of the thigh or buttock;
d. reading the number corresponding to the identified photograph; wherein utilizing the scales produces a consistency among evaluators of at least 50%.

In other embodiments, when the CR-PCSS scale is employed by a plurality of clinicians, at least 40% of the clinicians gave the patients the same rating from when the patients were screened and Day 1 of treatment. Or, such clinicians provided such same rating in at least about 50%, or about 60%, or about 70%, or about 80%, or about 90% or about 100% of patients.

2. Clinician Use of CR-PCSS

In practice, if the clinician is evaluating either the left buttock or right buttock, then the CR-PCSS buttock scale (FIGS. 5A-5E)) is used. If either the left posterolateral thigh or right posterolateral thigh is evaluated, then the CR-PCSS thigh scale (FIGS. 3A-3E) is used. The clinician next determines which picture of cellulite with label and descriptor on the CR-PCSS is most similar to the cellulite in the quadrant under evaluation. The matching of the scale to the patient may be done live or by the clinician analyzing images. The cellulite severity score that most closely approximates the quadrant's cellulite is assigned to the quadrant for the particular visit. In one embodiment, if a clinician feels that the patient's quadrant is exactly in the middle of two severity levels, then the clinician will choose the higher severity level.

In another embodiment, digital images of a quadrant are taken with a high quality digital camera (e.g., Canfield Scientific's VECTRA 3-D camera). The digital images are then shown on a high-resolution monitor. Images of a quadrant then appear one at a time, and the clinician will evaluate the image and rate its cellulite severity before moving onto evaluating the next image. In lieu of digital images, other images (e.g., photographs) are evaluated and rated.

3. Patient Use of PR-PCSS

In practice, if the patient is evaluating either her left buttock or right buttock, then the PR-PCSS buttock scale (FIGS. 4A-4E) is used. If either the left posterolateral thigh or right posterolateral thigh is evaluated, then the PR-PCSS thigh scale (FIGS. 2A-2E) is used. The patient next determines which picture of cellulite with label and descriptor on the PR-PCSS is most similar to the cellulite in the quadrant under evaluation. The matching of the score to the quadrant may be done live (via mirrors) or by analyzing images. The cellulite severity score that most closely approximates the quadrant's cellulite is assigned to the quadrant for the particular visit. In one embodiment, if the patient feels that her quadrant is exactly in the middle of two severity levels, then the patient will choose the higher severity level.

METHODS OF TREATMENT, THERAPEUTIC ENDPOINTS AND EFFICACY

The present disclosure provides a method of treating cellulite in a human patient in need thereof, comprising: (a) providing a pharmaceutical formulation comprising a mixture of collagenase I and collagenase II obtained or derived from *Clostridium histolyticum* wherein the mixture has a specific activity of about 5,000 ABC units/mg to 25,000 ABC units/mg; and (b) injecting the pharmaceutical formulation to the collagenous septa network of cellulite at a dose of about 0.1 mg to 5 mg, wherein the patient has a ≥2-point improvement from baseline for the CR-PCSS at day 71 following treatment. Further, the ≥2-point improvement from baseline at day 71 may be shown for both the CR-PCSS and the PR-PCSS. In another aspect, such treatment may result in a ≥1-point or ≥3-point improvement from baseline for one or both the CR-PCSS and PR-PCSS at day 71 post-treatment. In addition, the ≥3-point, or ≥2-point, or ≥1-point improvement may be seen at about 6 months or about 12 months post-treatment with either or both the CR-PCSS and PR-PCSS. Further, such patients may have a ≥3-point, or ≥2-point, or ≥1-point improvement from baseline for both the CR-PCSS and PR-PCSS score at about 22 days, 43 days, 90 days, or 180 days after treatment. The improvement may be seen at about 15 days, 25 days, 35 days, 45 days, 55 days, 65 days, 75 days, 85 days, or 95 days post-treatment.

The above-described treatment method may comprise about 1 to 10 treatment sessions or about 2 to 5 treatment sessions, or about 3 treatment sessions. Each treatment session may comprise administering the mixture of collagenase I and II as the sole active ingredients in the pharmaceutical formulation. The collagenase I and II may be present in an approximate ratio of 1:1 or other ratio described above. Each of the collagenase I and II may have a purity by area of at least 80% as measured by RP-HPLC, or at least 85%, or at least 90%, or at least 95%, or at least 100% as measured by RP-HPLC. Alternatively, other scales described herein may be substituted for the CR-PCSS and PR-PCSS to assess the effectiveness of therapy and improvement of cellulite appearance at day 71, at 6 months, or at 12 months following one or more treatment sessions.

Such treatment may be performed on a statistically significant population of human patients, particularly females, where such patients demonstrate a statistically significant improvement as measured by a ≥2-point improvement in both the CR-PCSS and PR-PCSS scores. The percentage of patients experiencing such improvement may be at least 10%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%. Similar percentages of improvement may also be seen in patients demonstrating a ≥1-point or ≥3-point improvement in both CR-PCSS and PR-PCSS at day 71, or 6 months, or 12 months after treatment. The treatment also shows a statistically significant improvement in a population of patients when measured at day 71, 6 months, or 12 months post-treatment utilizing one or more of the GAIS, the CSI, the SR-CIS, the SCTA, the SGA-C, the GAIS-C, S-GAIS and I-GAIS.

In another embodiment, patients will receive up to three treatment visits of injections of CCH (0.84 mg/treatment area, two treatment areas per visit) with each treatment visit occurring approximately 21 days apart. Twelve injections are administered into cellulite dimples during each visit across each affected area—the left and right buttock. At both the outset and conclusion of treatment, cellulite severity is assessed by each patient and clinician using two validated photonumeric cellulite severity scales, e.g., CR-PCSS and PR-PCSS. A primary endpoint is a composite responder analysis demonstrating at least a 2-level composite improvement, independently reported by both patient and clinician on the photonumeric scales of cellulite severity. Key secondary endpoints may include the percentage of subjects that experience at least a 1-level or 2-level improvement in patient reported assessment, percentage of subjects with a 1-level composite improvement, percentage of satisfied subjects, change from baseline in a cellulite impact scale, i.e., patients' self-perception related to their cellulite, as well as the percentage of subjects with at least a 1-level or 2-level improvement in the global aesthetic improvement scale (GAIS). In another embodiment, a patient receives treatment to 1-4 affected areas per office visit.

In a further aspect, when the CR-PCSS is employed by a plurality of clinicians, at least 40% of clinicians give the patient's area of cellulite the same cellulite severity rating from when the patient was screened and day 1 pre-treatment. In other embodiments, at least 50%, 60%, 70%, 80%, 90%, or 100% of clinicians give the patient's area of cellulite the same cellulite severity rating from when the patient was screened and immediately before the first treatment session (i.e., day 1 pre-treatment). Such consistencies of ratings are also seen at a time point selected from the group consisting of screening, day 1 pre-treatment, day 30 post-treatment, day 60 post-treatment, day 120 post-treatment, day 180 post-treatment, and 12 months post-treatment. The plurality of clinicians may comprise 2-10 clinicians. Further, the CR-PCSS and PR-PCSS may be employed to assess cellulite severity by one or more of live assessment, by viewing digital images of the cellulite area, by viewing photographs of the cellulite area, and by viewing mirrored images of the cellulite area.

In one embodiment, the collagenase is injected into an affected area as illustrated in FIG. 7. The spacing of the injections can vary from between about 0.1 cm to about 15 cm, or about 1 cm to about 10 cm, or about 0.5 cm to about 2 cm.

Further, in certain embodiments, the inter-rater reliability between clinicians and subjects between CR- and PR-PCSS may comprise:
  Left buttock (minor or photo): about 0.2 to about 0.8 for ICC (C,1) and about 0.2 to about 0.8 for ICC (A,1)
  Right buttock (mirror or photo): about 0.2 to about 0.8 for ICC (C,1) and about 0.2 to about 0.8 for ICC (A,1).
  Left thigh (mirror or photo): about 0.3 to about 0.9 for ICC (C,1) and about 0.1 to about 0.8 for ICC (A,1).
  Right thigh (mirror or photo): about 0.3 to about 0.9 for ICC (C,1) and about 0.2 to about 0.3 for ICC (A,1).

In other embodiments, the intra-rater reliability using CR-PCSS, clinicians agreed with themselves about 40% to about 90% of the time for buttock ratings. For thigh ratings, they agreed about 40% to about 90% of the time. The intra-rater ICCs for left and right buttocks range from abut 0.6 to 0.95 (ICC (A,1)) with a 95% CI of about 0.6 to 0.95. For thigh areas, the ICCs range from about 0.6 to 0.95 (ICC(A,1)) with a 95% CI of about 0.6 to 0.95.

The CR-PCSS inter-rater reliability shows agreement of about 60% to 95% of clinicians for both thigh and buttock areas. ICCs may range from about 0.5 to about 0.9 (ICC (A,1)).

In another aspect, the treatment method evaluates the durability of the effect of 2-level composite responders (patients that had an improvement of at least 2 levels of cellulite severity in both the PR-PCSS and the CR-PCSS), resulting in a statistically significant number demonstrated durability of effect at 6 months and 12 months. In certain embodiments, at least about 30%, or 35%, or 40%, or 45%, or 50%, or 55%, or 60%, or 65%, or 70%, or 75%, or 80%, or 85%, or 90%, or 95%, or 100% of patients demonstrate such durability.

EXAMPLES

The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the invention. Therefore all matter set forth is to be interpreted as illustrative and not in a limiting sense.

Example 1—Efficacy and Safety of CCH for the Treatment of EFP

In a Phase 2a clinical trial of CCH for the treatment of cellulite, Applicant demonstrated that three doses of CCH (XIAFLEX®) (low (0.06 mg), mid (0.48 mg) and high (0.84 mg)) showed an improvement in the appearance of cellulite as measured by the trial endpoints of an investigator and a patient score on the Global Aesthetic Improvement Scale (GAIS), which was adapted for use in cellulite. The mid- and high-dose groups demonstrated a statistically significant improvement in the appearance of cellulite, as measured by GAIS scores, with a p-value of <0.05 compared to placebo for both endpoints. In the mid and high dose groups, 68 percent of patients reported being "Satisfied" or "Very Satisfied" with the results of their treatment, compared to only 34 percent of patients randomized to placebo. CCH was well-tolerated by all dose groups with most adverse events (AEs) being mild to moderate and primarily limited to the local injection area.

Applicant next performed a Phase 2b clinical trial enrolling 375 women with moderate or severe cellulite aged 18 years or older in the United States. Each subject received up to three treatment sessions of CCH (0.84 mg/session) or placebo with each treatment session occurring approximately 21 days apart. Twelve injections were administered into cellulite dimples during each session across an entire treatment quadrant—left or right buttock or left or right posteriolateral thigh. At both the outset and conclusion of the study period (28 days after the last treatment), cellulite severity was assessed by each patient and clinician using two photonumeric cellulite severity scales—the PR-PCSS and CR-PCSS scales described above. Patient demographics and other information included:
  Moderate or severe EFP on left or right buttock or posterolateral thigh
    CR-PCSS and PR-PCSS scores of 3 to 4 in ≥1 quadrant and a Hexsel CSS total score ≤13
  No history of keloidal scarring or abnormal wound healing
  No active cutaneous alteration in the area to be treated (e.g., rash, eczema, skin cancer)
  No liposuction on side of body selected during previous 12 months
  None of the following in treatment quadrant selected:
    Injection (e.g., mesotherapy), laser therapy, or surgery during previous 12 months
    Endermologie during previous 6 months
    Massage therapy during previous 3 months
    Creams for EFP during previous 2 weeks More specifically, the patient populations and demographics were as follows: 375 patients enrolled (mean age, 46.5 yr; 86.4% white)

TABLE 23

| Population | CCH 0.84 mg | Placebo |
|---|---|---|
| ITT (safety),* n | 189 | 186 |
| mITT,† n | 177 | 184 |
| Parameter (ITT population) | | |
| Mean age, yr (range) | 47.2 (18-69) | 45.8 (19-70) |
| Race, n (%) | | |
| White | 167 (88.4) | 157 (84.4) |
| Black | 15 (7.9) | 26 (14.0) |
| Other | 7 (3.7) | 3 (1.6) |
| BMI category, n (%) | | |
| Underweight (<18.5 kg/m$^2$) | 2 (1.0) | 1 (0.5) |
| Normal (18.5 to < 25 kg/m$^2$) | 51 (27.0) | 50 (26.9) |
| Overweight (25 to < 30 kg/m$^2$) | 68 (36.0) | 72 (38.7) |
| Obese (≥30 kg/m$^2$) | 68 (36.0) | 63 (33.9) |

* All randomly assigned patients who received ≥ 1 injection of study medication.
† All patients in ITT population who had ≥ 1 post-injection CR-PCSS and PR-PCSS score.
BMI = body mass index;
CCH = collagenase clostridium histolyticum;
ITT = intent-to-treat;
mITT = modified intent-to-treat.

Figure 8:
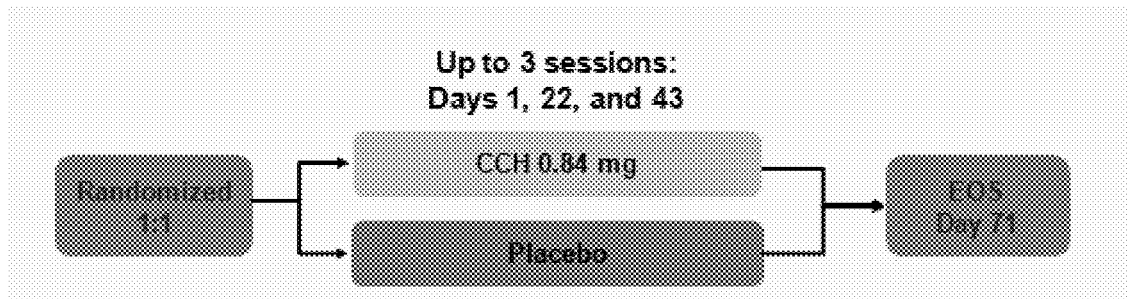
FIG. 8 is a schematic of a study design.

The Phase 2b trial was randomized, double-blind and placebo-controlled. The primary endpoint was the proportion of composite responders at Day 71 defined as subjects with a 2-point improvement in severity from baseline in the clinician-reported (CR-PCSS) and a 2-point improvement in the patient-reported (PR-PCSS). Additional endpoints include a composite of 1-point responders, the percentage of responders with 1-point and 2-point improvements on the CR-PCSS and PR-PCSS, assessment of improvement by patient and clinician using the Global Aesthetic Improvement Scale (GAIS); subject satisfaction, and change in the Hexsel Cellulite Severity Scale. Adult women who had moderate to severe edematous fibrosclerotic panniculopathy on at least 1 quadrant of their right or left buttock or posterolateral thigh were included. Quadrants were randomly assigned if the patient had more than one eligible quadrant. Patients were randomized 1 to 1 to receive either placebo or collagenase *Clostridium histolyticum* (EN3835 or XIAFLEX®) 0.84 mg injections into dimples in the selected quadrant. Patients could receive up to 3 treatment sessions. Each treatment session comprised 12 injections (0.3 mL) of XIAFLEX® in the selected quadrant. Each session was approximately 21 days apart. FIG. 8 is a schematic of the study design.

The primary endpoint was the percentage of composite responders (defined as an individual with a ≥2-point improvement from baseline for both the Clinician-Reported Photonumeric Cellulite Severity Scale and the Patient-Reported Photonumeric Cellulite Severity Scale score) at Day 71.

A secondary endpoint was the percentage of composite responders (defined as an individual with a ≥1-point improvement from baseline for both the Clinician-Reported Photonumeric Cellulite Severity Scale and the Patient-Reported Photonumeric Cellulite Severity Scale score) at Day 71.

Investigator-Global and Subject-Global Aesthetic Improvement Scales and Hexsel Cellulite Severity Scale were assessed at Day 71.

Of 489 patients screened, 189 were randomly assigned to receive collagenase *Clostridium histolyticum* (CCH) 0.84 mg and 186 to receive placebo and had at least 1 injection (safety and intent-to-treat [ITT] populations).

The primary endpoint (i.e., percentage of patients who had ≥2-point improvement from baseline in Clinician-Reported Photonumeric Cellulite Severity Scale [CR-PCSS] and Patient-Reported Photonumeric Cellulite Severity Scale [PR-PCSS] score) was evaluated in the ITT population.

All secondary efficacy analyses were performed in the modified intent-to-treat population (ie, randomly assigned patients who received at least 1 injection and had at least 1 post-injection CR-PCSS and PR-CSS score).

In the ITT population, mean patient age, race, and body mass index category were similar in the CCH and placebo groups. In the intent-to-treat population:
A statistically greater percentage of patients who received collagenase *Clostridium histolyticum* (CCH) had a ≥2-point improvement in both Clinician- and Patient-Reported Photonumeric Cellulite Severity Scale score at day 71 compared with placebo (primary endpoint; P<0.001)
A statistically greater percentage of patients who received CCH had a ≥1-point improvement in both Clinician- and Patient-Reported Photonumeric Cellulite Severity Scale score at day 71 compared with placebo (secondary endpoint; P<0.001)
At day 71, statistically significantly greater improvements in various investigator and patient scales were observed with collagenase *Clostridium histolyticum* versus placebo (P<0.001 for all)
A greater percentage of patients who received collagenase *Clostridium histolyticum* (CCH; 82.0%) reported a treatment-emergent adverse event (AE) than those who received placebo (26.9%), but most AEs in the CCH group were mild in intensity (65.7% [468/712]; intensity data not shown)
Only approximately 4% of AEs caused patients to discontinue CCH treatment
Treatment-related AEs occurred in 81.5% of patients in the CCH group and 18.3% of patient in the placebo group
The most common treatment-related AEs in both groups were injection site bruising (CCH, 75.1%; placebo, 12.9%) and injection site pain (CCH, 59.3%; placebo, 5.4%)
Treatment with CCH significantly improve clinician and patient ratings of EFP appearance versus placebo
Key Phase 2b trial results further included:
Subjects receiving CCH demonstrated a highly statistically significant improvement in the primary endpoint of composite investigators' and patients' assessments of the appearance of cellulite, as measured by a two-point improvement in both the CR-PCSS and PR-PCSS scores, with a p-value of <0.001 versus placebo
Subjects receiving CCH demonstrated a highly statistically significant improvement in the composite investigators' and patients' assessments of the appearance of cellulite, as measured by a one-point improvement in both the CR-PCSS and PR-PCSS scores, with a p-value of <0.001 versus placebo
A highly significant proportion of CCH subjects reported being "Satisfied" or "Very Satisfied" with their cellulite treatment, compared to placebo subjects, with a p-value of <0.001
A highly significant proportion of CCH subjects were reported as "Improved" or "Very Improved" or "Very Much Improved" in global appearance of their cellulite area as assessed by the subjects and investigators, compared to placebo subjects, with a p-value of <0.001

CCH was well-tolerated by all dose groups with most adverse events (AEs) being mild to moderate and primarily limited to the local injection area; 92 percent of all related AEs were mild to moderate in the CCH group compared to 96 percent in the placebo group; the most common AEs were expected and included injection site bruising (approximately 75 percent) and injection site pain (approximately 59 percent)

Figure 6A:
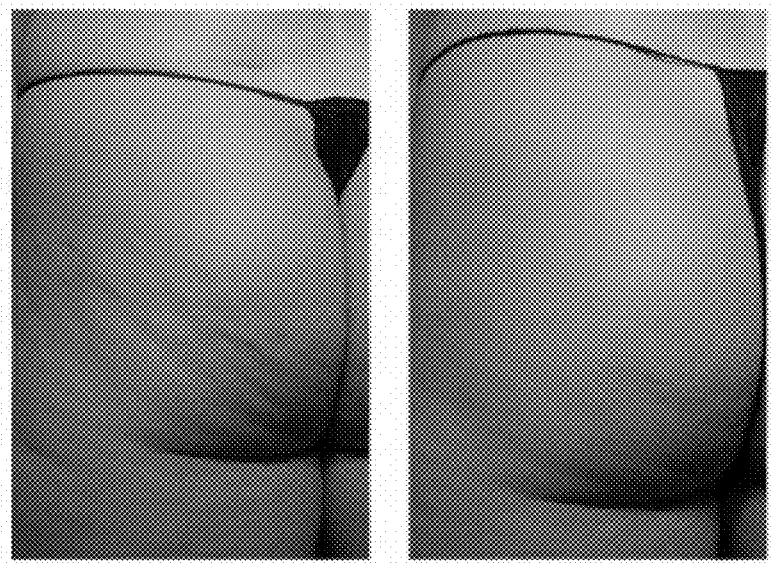
FIGS. 6A and 6B are a series of photographs depicting pre- and post-treatment of cellulite in the buttock of two patients treated with CCH or placebo, respectively, and having a response of 2-point improvement in CR-PCSS and PR-PCSS ratings or no change in ratings, respectively.
Figure 6B:
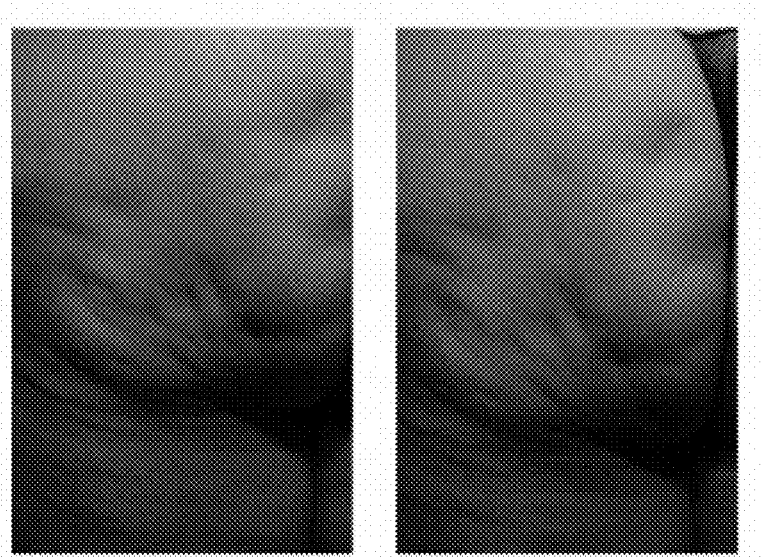

FIGS. 6A and 6B are a series of photographs depicting pre- and post-treatment of cellulite in the buttock of two patients treated with CCH or placebo, respectively, and having a response of 2-point improvement in CR-PCSS and PR-PCSS ratings or no change in ratings, respectively.

Figure 9:
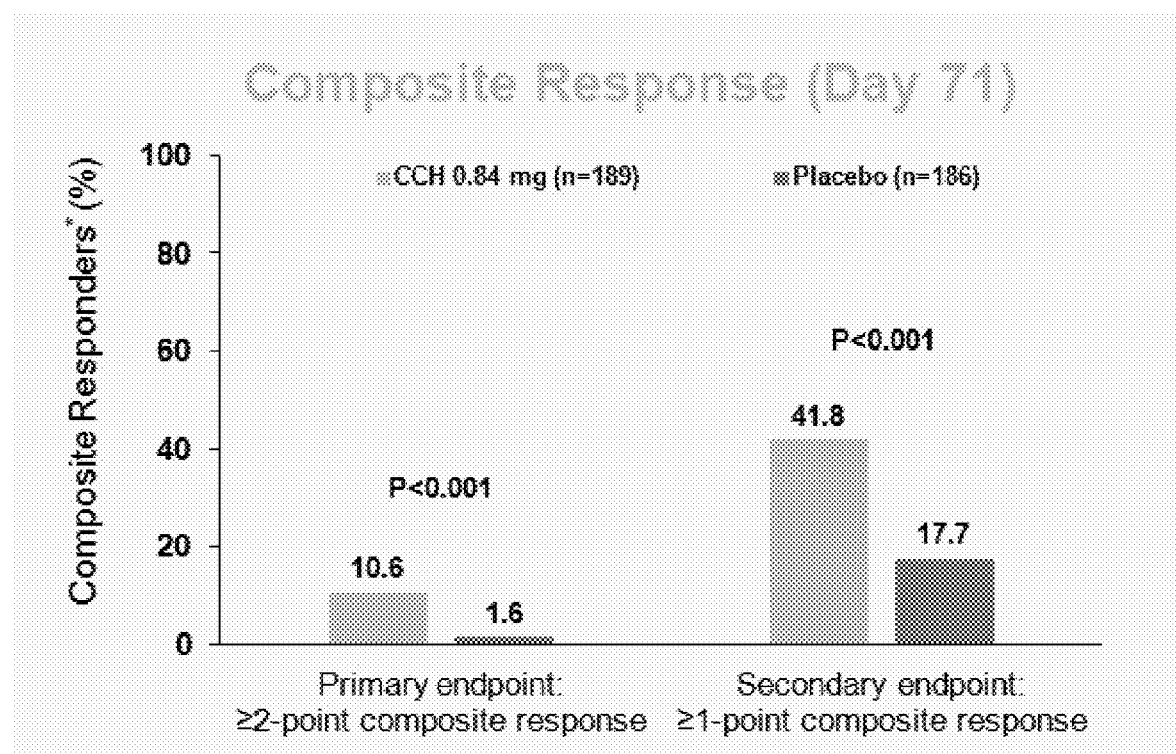
FIG. 9 is a graph reporting the composite response at day 71 following CCH or placebo therapy of a primary and a secondary endpoint.

FIG. 9 is a graph reporting the composite response at day 71 following CCH therapy or placebo of a primary and a secondary endpoint.

Figure 10A:
FIGS. 10A and 10B are a series of photographs depicting pre- and post-treatment of cellulite in the buttock of a patient treated with CCH, and showing a 2-point composite response from baseline assessment.
Figure 10B:

FIGS. 10A and 10B are a series of photographs depicting pre- and post-treatment of cellulite in the buttock of a patient treated with CCH, and showing a 2-point composite response from baseline assessment.

Figure 11A:
FIGS. 11A and 11B are a series of photographs depicting pre- and post-treatment of cellulite in the buttock of a patient treated with CCH, and showing a 1-point composite response from baseline assessment.
Figure 11B:
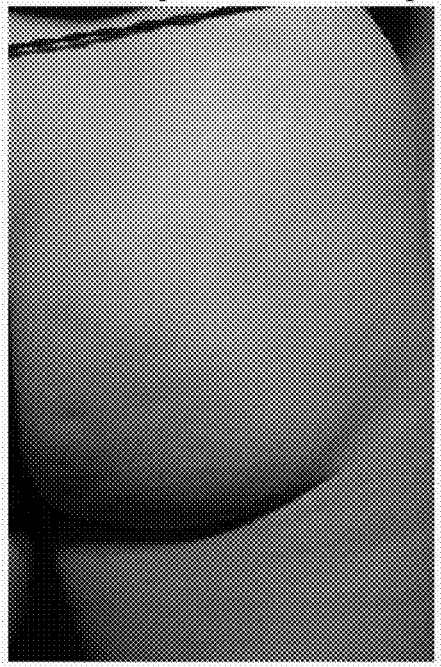

FIGS. 11A and 11B are a series of photographs depicting pre- and post-treatment of cellulite in the buttock of a patient treated with CCH, and showing a 1-point composite response from baseline assessment.

Figure 12A:
FIGS. 12A and 12B are a series of photographs depicting pre- and post-treatment of cellulite in the buttock of a patient treated with CCH, and showing a 1-point response based on the PR-PCSS.
Figure 12B:

FIGS. 12A and 12B are a series of photographs depicting pre- and post-treatment of cellulite in the buttock of a patient treated with CCH, and showing a 1-point response based on the PR-PCSS.

Figure 13A:
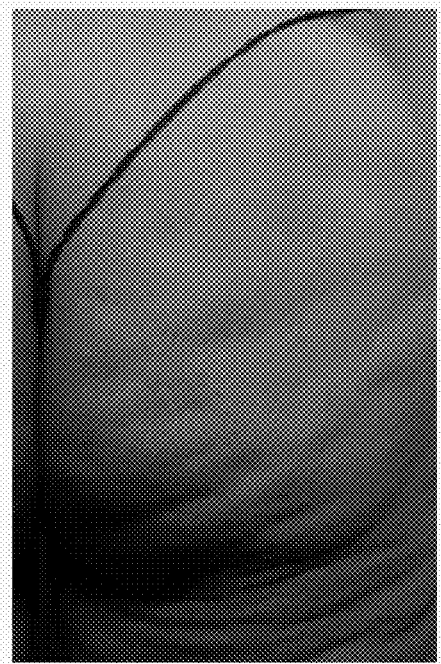
FIGS. 13A and 13B are a series of photographs depicting pre- and post-treatment of cellulite in the buttock of a patient treated with placebo, and showing no change in CR-PCSS or PR-PCSS scores.
Figure 13B:
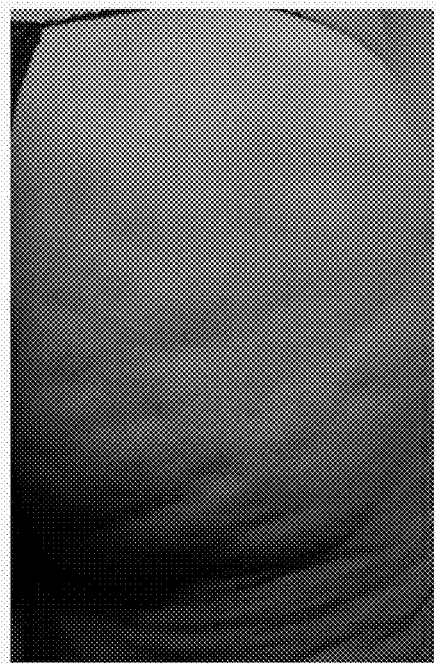

FIGS. 13A and 13B are a series of photographs depicting pre- and post-treatment of cellulite in the buttock of a patient treated with placebo, and showing no change in CR-PCSS or PR-PCSS scores.

Overall, CCH treatment was generally well tolerated
Low (3.7%) rate of patient discontinuations due to AEs
Further clinical evaluation of CCH for EFP (cellulite) is warranted Other efficacy measures and further details on safety profiles are provided in the following tables.

TABLE 24

Other Efficacy Measures*

| Parameter | CCH 0.84 mg (n = 177) | Placebo (n = 184) | P Value |
|---|---|---|---|
| Patients with ≥ 1 level improvement from baseline at day 71, n (%) | | | |
| CR-PCSS | 96 (54.2) | 53 (28.8) | <0.001 |
| PR-PCSS | 128 (72.3) | 95 (51.6) | <0.001 |
| I-GAIS | 110 (62.9) | 60 (32.8) | <0.001 |
| S-GAIS | 128 (73.1) | 80 (43.7) | <0.001 |
| Mean change from baseline at day 71 (SD) | | | |
| Hexsel CSS | −1.7 (2.2) | −0.9 (2.0) | <0.001 |

*mITT population using LOCF analysis.
CCH = collagenase clostridium histolyticum;
CSS = Cellulite Severity Scale;
I-GAIS = Investigator-Global Aesthetic Improvement Scale;
LOCF = last observation carried forward;
mITT = modified intent-to-treat;
S-GAIS = Subject-Global Aesthetic Improvement Scale.

TABLE 25

Safety Profile

| Patients With an AE, n (%) | CCH 0.84 mg (n = 189) | Placebo (n = 186) |
|---|---|---|
| Any AE | 183 (81.0) | 33 (17.7) |
| Any treatment-related AE | 154 (81.5) | 34 (18.3) |
| Treatment-related AEs (>5% in either group) | | |
| Injection site bruising | 142 (75.1) | 23 (12.4) |
| Injection site pain | 112 (59.3) | 10 (5.4) |
| Injection site nodule | 27 (14.3) | 0 |
| Injection site pruritus | 21 (11.1) | 1 (0.5) |
| Injection site swelling | 14 (7.4) | 1 (0.5) |
| Injection site induration | 11 (5.8) | 0 |
| Injections site mass | 10 (5.3) | 1 (0.5) |
| Discontinuation due to AE | 7 (3.7) | 1 (0.5) |

Most (92.3%) of the AEs in the CCH group were mild or moderate in intensity CCH = collagenase clostridium histolyticum; AE = treatment-emergent adverse event.

The results from the Phase 2b study demonstrated that treatment (3 visits approximately 21 days apart) improved the cellulite severity of the treatment area as assessed by the primary endpoint of 2-level composite responder analyses, the proportion of responders based on an improvement of ≥2 levels in the appearance of cellulite in both the patient PR-PCSS and the clinician CR-PCSS of buttocks and thighs was statistically significantly greater in subjects who received EN3835 0.84 mg (10.6%; p<0.001) compared to subjects who received placebo (1.6%); 1-level (or greater) responders in the PR-PCSS of EN3835-treated subjects (72.3%) was significantly greater than 1-level responders in the placebo group (51.6%) (p<0.001); statistically significant (p≤0.001) improvement in the appearance of cellulite based on the subject S-GAIS were observed in EN3835 0.84-mg group (73.1%) compared to the placebo group (44.0%); and 62.9% of subjects in the EN3835 0.84 mg group were satisfied or very satisfied with the results of their cellulite treatment compared with only 35.9% of subjects in the placebo group (p<0.001). In subjects treated in buttocks (n=187), the proportion of 2-level composite responders was statistically significantly greater in subjects who received EN3835 0.84 mg compared to subjects who received placebo; 1-level (or greater) responders in the PR-PCSS of EN3835-treated subjects was significantly greater than 1-level responders in the placebo group.

Additional evidence for reliability and validity of the CR-PCSS and PR-PCSS analyzed statistically, which supported the reliability and validity of the CR-PCSS and PR-PCSS. More particularly, the agreement between right and left buttocks shows that both scales can be used to produce very high levels of agreement, with the clinician results showing higher agreement (i.e., about 5%, 10%, 15%, 20%, 30% higher than patients using the PR-PCSS). Clinicians showed good inter-rater reliability on ratings. These results support the use of the CR-PCSS and CR-PCSS instruments as endpoints for treating cellulite.

Figure 14:
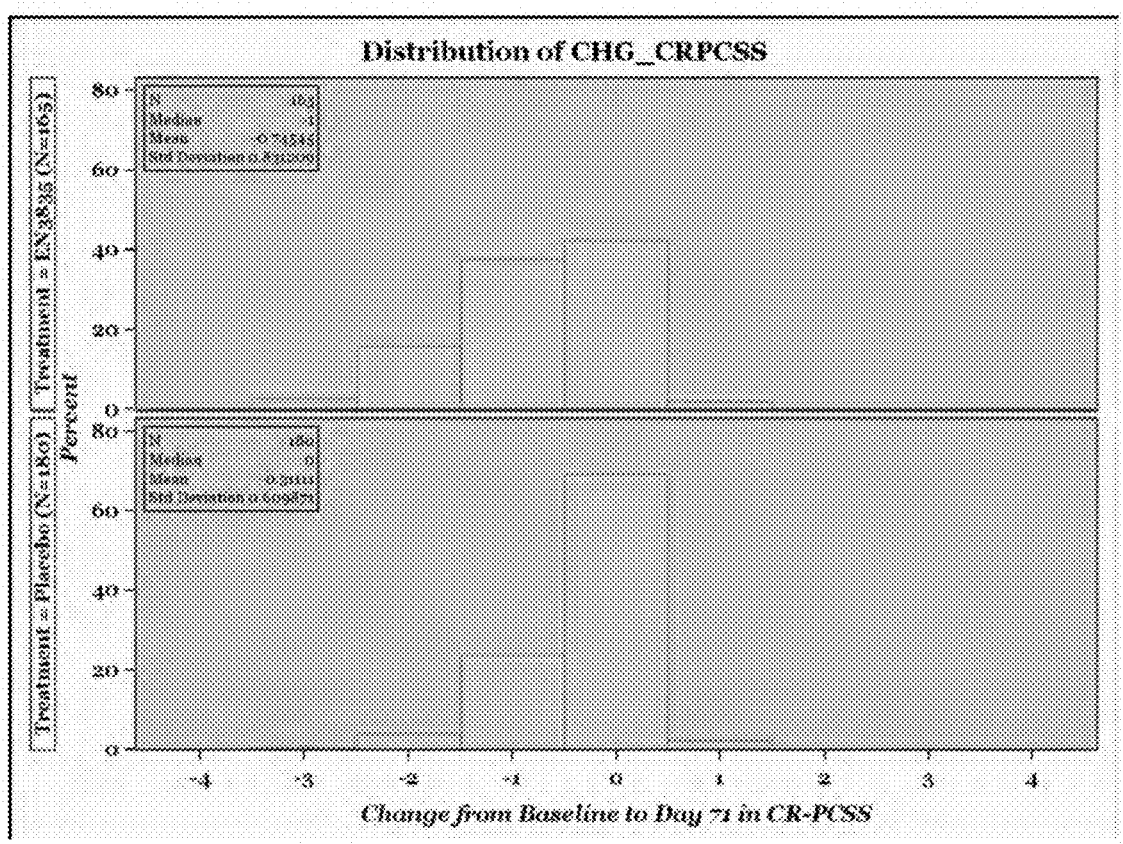
FIG. 14 is a bar graph showing the probability distribution for change from baseline to Day 71 in CR-PCSS by treatment group based on all available data from the phase 2b study.
Figure 15:
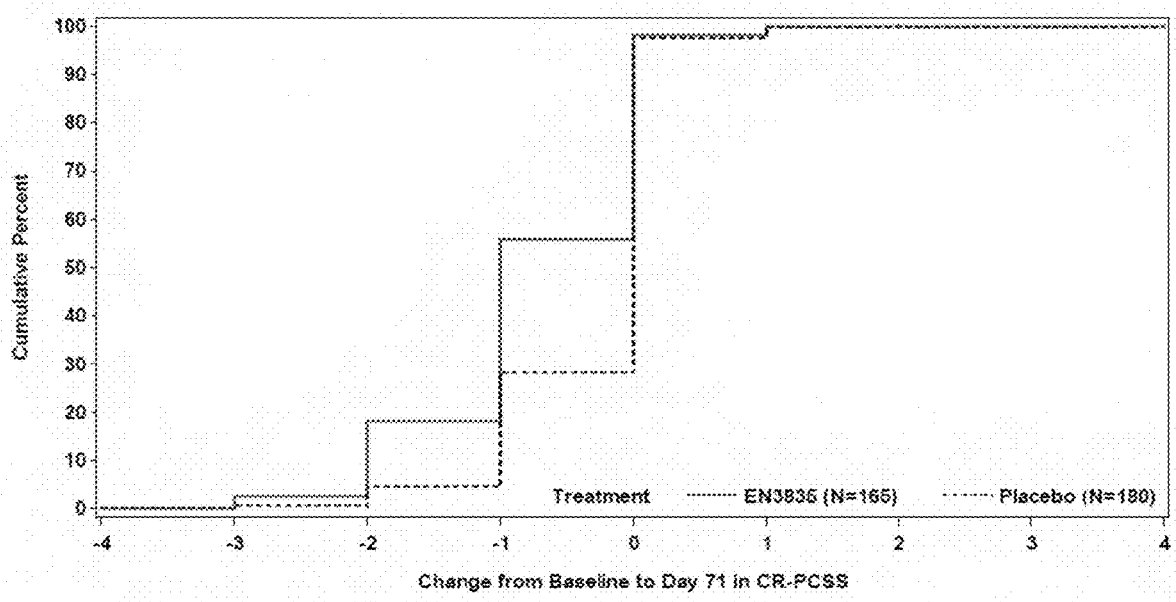
FIG. 15 is a bar graph showing the cumulative distribution function (CDF) for change from baseline to Day 71 in CR-PCSS by treatment group based on all available data from the phase 2b study.
Figure 16:
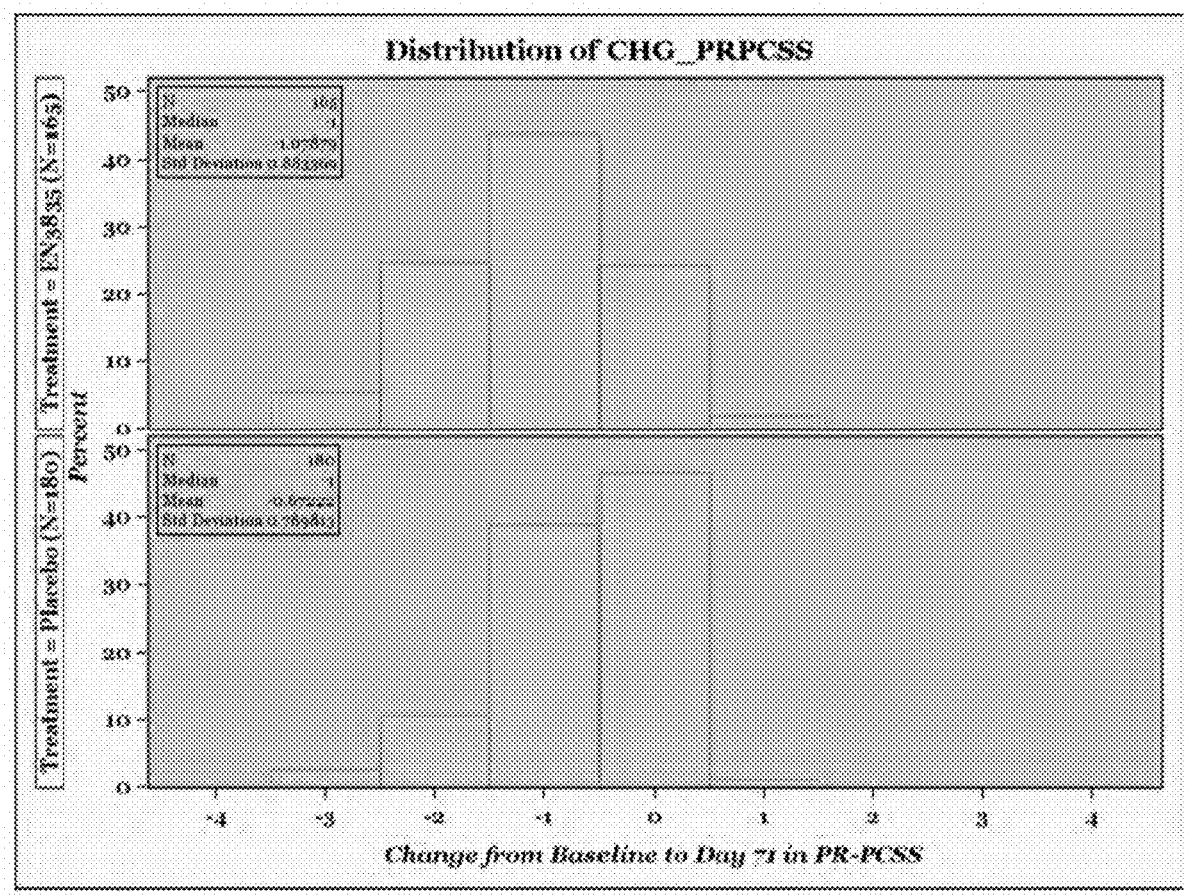
FIG. 16 is a bar graph showing the probability distribution for change from baseline to Day 71 in PR-PCSS by treatment group based on all available data from the phase 2b study.
Figure 17:
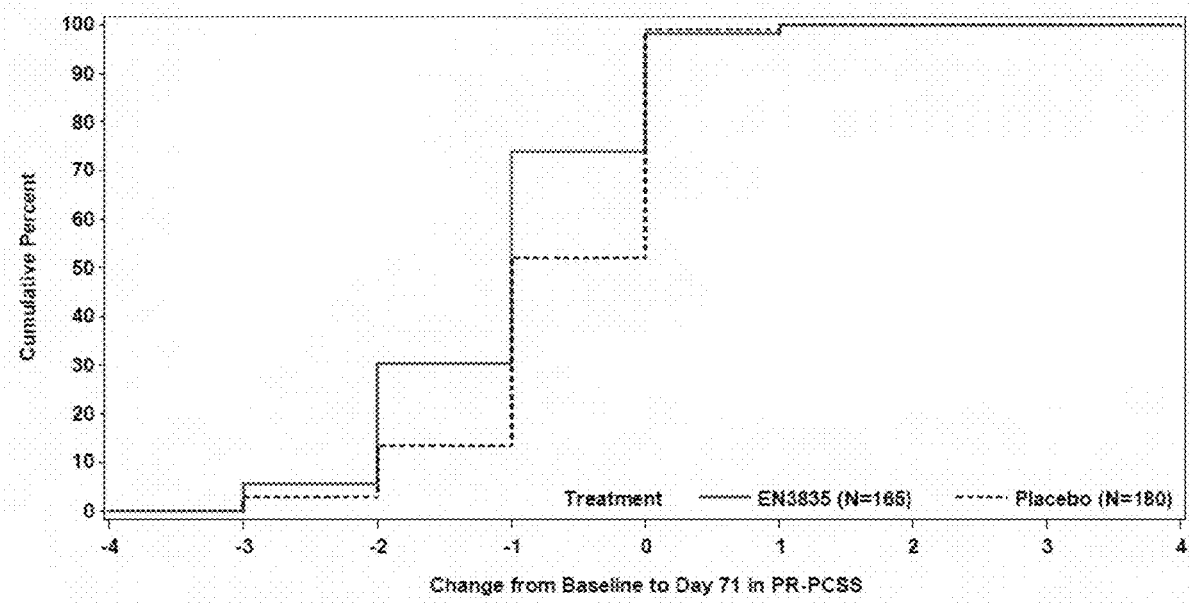
FIG. 17 is a bar graph showing the cumulative distribution function (CDF) for change from baseline to day 71 in PR-PCSS by treatment group based on all available data from the phase 2b study.

Further, FIGS. 14 and 15 show that EN3835-treated subjects have a higher probability to achieve a change of −3, −2, −1 (cellulite severity reduced by 3 levels, 2 levels or 1 level, respectively) on CR-PCSS at Day 71 than placebo-treated patients. Active treatment resulted in a higher percentage of patients across all levels of change score providing for clinical effectiveness of EN3835. Likewise, FIGS. 16 and 17 show that EN3835-treated subjects have a higher probability to achieve a change of −3, −2, −1 (cellulite severity reduced by 3 levels, 2 levels or 1 level, respectively) on PR-PCSS at Day 71 than placebo-treated patients. Active treatment resulted in a higher percentage of patients across all levels of change score providing for clinical effectiveness of EN3835.

The study also demonstrated EN3835 to be well tolerated with no serious adverse events (SAES) related to EN3835. Safety results from a total of 4 studies (1 pilot, 2 Phase 1, and 2 Phase 2 studies) in which 435 adult females received subcutaneous injections of EN3835 indicate that the majority of treatment-emergent adverse events (TEAEs) are transient, non-serious, mild or moderate in intensity, and related to the local administration of EN3 835. The immunogenicity profile after 3 treatment visits of EN3835 indicate that greater than 90% of EN3835-treated subjects were seropositive for Collagenase I and/or Collagenase II antibodies; this profile of EN3835 is similar to that observed in the Dupuytren's contracture and Peyronie's disease programs.

Example 2—Comparisons of Clinician-Reported and Patient-Reported Cellulite Severity Scales With Existing Scales for Measurement of Cellulite Severity The Hexsel Cellulite Severity Scale (CSS) is a current evaluation tool to measure cellulite severity. The Hexsel CSS rates each of 5 domains of cellulite (number of evident depressions, depression depth, morphologic skin surface alterations, skin laxity, flaccidity, or sagging, and Nünberger and Müller classification) from "0" (no alteration) to "3" (most severe).

In a phase 2 trial, adult women with edematous fibrosclerotic panniculopathy (cellulite) rated 4 anatomical quadrants of the buttocks and posterolateral thighs at screening using the PR-PCSS. Clinicians assessed the same 4 quadrants and reported cellulite severity using the CR-PCSS and the Hexsel CSS. Patients who had ≥1 quadrant with moderate or severe cellulite (i.e., CR-PCSS score of 3 or 4, PR-PCSS score of 3 or 4, and Hexsel CSS score ≤13) at screening and Day 1 were randomly assigned to receive a pharmacologic treatment or placebo in 1 cellulite quadrant. The CR-PCSS, PR-PCSS, and Hexsel CSS were completed at screening and at Days 1, 22, 43, and 71. The Subject Global Aesthetic Improvement Scale (S-GAIS), which assesses patient-rated improvement in cellulite from 3 ("very much improved") to −3 ("very much worse"), was completed at Day 71. Agreements between CR-PCSS and Hexsel CSS, between CR-PCSS and PR-PCSS, and between mean changes in PR-PCSS from Day 1 to Day 71 and S-GAIS score at Day 71 were evaluated using Spearman rank correlation.

A total of 375 patients were randomized to treatment and received ≥1 treatment sessions (intent-to-treat population [ITT]). Ratings on the CR-PCSS, PR-PCSS, and Hexsel CSS at screening (N=1500) were included in correlation calculations. CR-PCSS scores significantly correlated with Hexsel CSS total scores overall (P<0.001) and in the thighs (P<0.001) and buttocks (P<0.001). Significant correlations between clinician and patient rating scales (CR-PCSS and PR-PCSS) were also observed overall (P<0.001) and within each target area (P<0.001 for both). In patients in the modified ITT population (patients in the ITT with ≥1 post-injection CR-PCSS and PR-CSS assessment, n=352), mean changes in PR-PCSS score correlated with ratings of aesthetic change on the S-GAIS (P<0.001).

Based on the results of Applicant's investigations, the CR-PCSS is an easier way for physicians to evaluate cellulite (i.e., single item) than the 5-domain Hexsel scale). Positive correlations between CR-PCSS and Hexsel CSS total scores and between PR-PCSS and S-GAIS support the validity of CR-PCSS and PR-PCSS in terms of standard scales (Hexsel CSS and S-GAIS). PR-PCSS correlated to the CR-PCSS (P<0.001), indicating that the 2 scales evaluated the disease state similarly (i.e., static evaluations of cellulite severity).

Example 3—Assessing Cellulite Severity: Test-Retest Reliability and Concordance Between New Clinician Reported and Patient Reported Photonumeric Scales Background: The Clinician Reported Photonumeric Cellulite Severity Scale (CR-PCSS) and Patient Reported Photonumeric Cellulite Severity Scale (PR-PCSS) are tools to allow reliable, efficient assessment of cellulite severity. The aim of this noninterventional study was to evaluate intra- and inter-rater reliability of the CR-PCSS in live ("in person") patients as assessed by clinicians, and its concordance with PR-PCSS.

Methods: The CR-PCSS and the PR-PCSS are 5-point photonumeric scales that include 5 photographs ranked in increasing order of cellulite severity, according to the number and depth of dimples on the evaluated area: left or right buttock (buttocks scale), or left or right posterolateral thigh (thighs scale), with corresponding labels (0=none, 1=almost none, 2=mild, 3=moderate, 4=severe) and text descriptors. Test-retest reliability of the CR-PCSS was evaluated at baseline and Day 2. To minimize clinician reliance on memory, patient order was changed on Day 2 and clinicians were not permitted visual or vocal cues, or touching of patients. The same patients included in clinician assessment of the CR-PCSS used the PR-PCSS to self-rate cellulite severity, using either photos or mirrors at baseline and the other method 14 days later; method order was randomly assigned. Intra- and inter-rater (CR-PCSS) reliability were estimated using intraclass correlation coefficients for agreement (ICC), and corresponding 95% confidence intervals (CI) were calculated. Concordance of the CR-PCSS with PR-PCSS ratings was calculated for the left or right buttock and left or right thigh at baseline.

Results: Six clinicians included as CR-PCSS raters were predominantly male (n=5; 83.3%), had practiced medicine for a mean of 21.3 years (range, 4-54 years), and specialized in plastic surgery (n=3; 50%) or dermatology (n=3; 50%). The 75 patients had a mean age of 44.8 years (range, 18-71 years) and were mostly White (n=52; 69.3%); the majority self-identified as having cellulite on both thighs and buttocks (n=57; 76%). The overall mean (95% CI) ICC point estimates for clinician intra-rater reliability of the CR-PCSS between baseline and Day 2 for both the left and right buttock were 0.81 (0.73, 0.90) and 0.81 (0.72, 0.90), and for the left and right thigh were 0.78 (0.67, 0.90) and 0.79 (0.67, 0.90), indicating reliability of ICCs across quadrants. At baseline, overall mean (95% CI) ICC point estimates for clinician inter-rater reliability for the left and right buttock were 0.76 (0.69, 0.83) and 0.76 (0.68, 0.82), and for the left and right thigh were 0.74 (0.67, 0.81) and 0.75 (0.68, 0.82). Intra- and inter-rater reliability for the CR-PCSS were considered within the acceptable range for all areas, with 95% CI lower-bound estimates near or above 0.70, and upper-bound estimates at approximately 0.90. At baseline, concordance (ICC [95% CI]) between the CR-PCSS and PR-PCSS (across methods) for the left and right buttock were 0.51 (0.32, 0.66) and 0.56 (0.38, 0.70), and for the left and right thigh were 0.61 (0.44, 0.73) and 0.67 (0.53, 0.78).

Conclusions: The CR-PCSS is a reliable tool for evaluating cellulite severity of the buttocks and thighs and correlates well with the PR-PCSS.

Example 4—Phase 3, Randomized, Double-Blind, Placebo-Controlled Trials of EN3835 in the Treatment of Edematous Fibrosclerotic Panniculopathy Two Phase 3 randomized, double-blind, placebo-controlled trials will be performed to assess the efficacy and safety of EN3835 in the treatment of EFP in about 420 adult women in each trial. Subjects will be screened for study eligibility within 14 days prior to enrolling in this study. Subjects with 2 treatment areas (bilateral buttocks) (also referred to as quadrants) with moderate or severe levels of cellulite as independently assessed by the subject using the Patient Reported Photonumeric Cellulite Severity Scale (PR-PCSS) and by the Investigator using the Clinician Reported Photonumeric Cellulite Severity Scale (CR-PCSS) will be eligible. The eligibility of the buttocks will be confirmed on Day 1. Once the eligibility of the buttocks is confirmed, subjects will be randomly assigned to a treatment group (EN3835 0.84 mg per buttock or placebo) in a 1:1 ratio within an investigational site. Each subject will receive a treatment course, which comprises of up to 3 treatment visits (sessions), separated by 21 days (i.e., Days 1, 22, and 43). Each treatment visit will consist of 12 injections (0.3 mL per injection of EN3835 0.07 mg/injection or placebo; 0.84 mg in 3.6 mL per buttock) in each of the two buttocks for a total volume of 7.2 mL (1.68 mg).

a. a score of 3 or 4 (moderate or severe) as reported by the subject (PR-PCSS), and
b. a score of 3 or 4 (moderate or severe) as reported by the Investigator (CR-PCSS)
4. At Day 1 visit, have 2 bilateral buttocks with each buttock having:
a. a score of 3 or 4 (moderate or severe) as reported by the subject (PR-PCSS), and
b. a score of 3 or 4 (moderate or severe) as reported by the Investigator (CR-PCSS).

A dose of 0.84 mg of EN3835 per buttock will be administered as 12 subcutaneous injections (0.3-mL injection administered as three 0.1-mL aliquots per injection) in each of two buttocks for a total dose of 1.68 mg and a total volume of 7.2 mL (3.6 mL per buttock). Total number of injections will be 24 injections per treatment visit into the two buttocks. There will be 3 treatment visits at 21 days intervals, i.e., treatments on Days 1, 22, and 43 will be administered.

Study drug will be injected subcutaneously. Each injection site will receive a single skin injection of study drug administered as three 0.1-mL aliquots to Positions A, B, and C (for a total injection volume of 0.3 mL) as shown in FIG. 7. During each treatment visit, 8 syringes (4 syringes per buttock) will be prepared for dosing. Each syringe will contain 0.9 mL of study drug (i.e., 3 injections in each syringe). Twelve (12) skin injections of 0.3 mL per injection will be administered within each of the two buttocks during each treatment visit.

As illustrated in FIG. 7, the drug administration at each injection site will be as follows:

TABLE 26

Study Treatment Groups

| Dose per Each Injection[a]/ Number of Subjects | Injection Volume per Each Injection | Number of Injections at Each Treatment Visit | Dose (mg) at Each Treatment Visit | Injection Volume (mL) per Each Treatment Visit | Cumulative EFP Dose |
|---|---|---|---|---|---|
| EN3835 0.07 mg/ N = 210 | 0.3 mL | 12 per buttock × 2 buttocks = 24 injections | 0.84 mg per buttock × 2 buttocks = 1.68 mg (12 injections per buttock × 0.07 mg/injection × 2 buttocks) | 3.6 mL per buttock × 2 buttocks = 7.2 mL (24 injections × 0.3 mL) | 5.04 mg (3 treatment visits × 0.84 mg per buttock × 2 buttocks) |
| Placebo/ N = 210 | 0.3 mL | 12 per buttock × 2 buttocks = 4 injections | — | 3.6 mL per buttock × 2 buttocks = 7.2 mL (24 injections × 0.3 mL) | — |

[a]Each injection of study drug is 0.3 mL administered as three 0.1 mL aliquots.

Subjects, investigators, site personnel, and Endo personnel will be blinded to the identification of the target and non target buttocks.

At Day 71 (End of Study/Early Termination), photographs of each of the buttocks will be taken and evaluated by subject using the PR-PCSS. The Investigator will conduct live assessments of each of the buttocks using the CR-PCSS. Global assessment evaluations will be completed by both the subject and the Investigator.

Inclusion criteria include:
1. Voluntarily sign and date an informed consent agreement
2. Be a female ≥18 years of age
3. At Screening visit, have 2 bilateral buttocks with each buttock having:

Needle Tip Position A: Position the needle at 90° angle perpendicular to the skin surface at the injection site and inject one 0.1 mL aliquot of study drug by gently pushing on the syringe plunger.

Needle Tip Position B: Withdraw the needle slightly (but not so much as to remove from the injection site) and reposition approximately 45° (but not more than 45°) off vertical and above the long axis of the dimple and inject one 0.1 mL aliquot of study drug) by gently pushing on the syringe plunger.

Needle Tip Position C: Withdraw the needle slightly (but not so much as to remove from the injection site) and reposition approximately 45° (but not more than 45°) off vertical and below the long axis of the dimple and inject one 0.1 mL aliquot of study drug by gently pushing on the syringe plunger.

Twelve (12) skin injections of 0.3 mL will be administered within each of the two treated buttocks during each treatment visit. The plane containing injection deposition points A, B, and C should be perpendicular to the skin and perpendicular to the long axis of a dimple if the dimple is an elongated trough-like dimple. After treatment, the subject will remain prone for at least 5 minutes. The total number of dimples treated and the total number of injections administered will be recorded during Treatment Visits 1, 2, and 3.

The duration of the study will be approximately 84 days (includes screening phase). The screening phase of the study will be up to 14 days.

Efficacy will be evaluated according to the following criteria for evaluation:
  i. Subject using PR-PCSS while viewing digital image of the target buttock: 5-level scale ranging from 0 (no cellulite) to 4 (severe cellulite) (Day 1 (Baseline) and Days 22, 43, and 71) for the target buttock
  ii. Subject using PR-PCSS while viewing digital image of the non-target buttock: 5-level scale ranging from 0 (no cellulite) to 4 (severe cellulite) (Day 1 (Baseline) and Days 22, 43, and 71) for the non-target buttock
  iii. Investigator using the CR-PCSS by live assessment: 5-level scale ranging from 0 (no cellulite) to 4 (severe cellulite) (Day 1 (Baseline) and Days 22, 43, and 71) for the target buttock
  iv. Investigator using the CR-PCSS by live assessment: 5-level scale ranging from 0 (no cellulite) to 4 (severe cellulite) (Day 1 (Baseline) and Days 22, 43, and 71) for the target buttock
  v. Investigator using the CR-PCSS by live assessment: 5-level scale ranging from 0 (no cellulite) to 4 (severe cellulite) (Day 1 (Baseline) and Days 22, 43, and 71) for the non-target buttock
  vi. Investigator Global Aesthetic Improvement Scale (I-GAIS): 7-level scale ranging from 3 (very much improved) to −3 (very much worse) (Days 22, 43, and 71) for the target buttock
  vii. Investigator Global Aesthetic Improvement Scale (I-GAIS): 7-level scale ranging from 3 (very much improved) to −3 (very much worse) (Days 22, 43, and 71) for the non-target buttock
  viii. Subject Global Aesthetic Improvement Scale (S-GAIS): 7-level scale ranging from 3 (very much improved) to −3 (very much worse) (Days 22, 43, and 71) for the target buttock
  ix. Subject Global Aesthetic Improvement Scale (S-GAIS): 7-level scale ranging from 3 (very much improved) to −3 (very much worse) (Days 22, 43, and 71) for the non-target buttock
  x. Patient Reported Cellulite Impact Scale (PR-CIS): 6 questions with responses to each question consisting of a numerical rating scale (NRS) ranging from 0 (Not at all) to 10 (Extremely)
  xi. Subject Self-Rating Scale (S SRS): 7-level scale ranging from 0 (extremely dissatisfied) to 6 (extremely satisfied) (Day 1 (Baseline) and Day 71)
  xii. Subject satisfaction with cellulite treatment assessment: 5-level scale ranging from 2 (very satisfied) to −2 (very dissatisfied) (Day 71) for both the target and non-target buttocks The primary endpoint is the proportion of 2-level composite responders at Day 71 defined as subjects with:
  i. an improvement in severity from baseline (Day 1 visit) of at least 2 levels of severity in the CR-PCSS as assessed live by the Investigator of the target buttock, and
  ii. an improvement in severity from baseline of at least 2 levels of severity in the PR-PCSS as assessed by the subject while viewing the digital image of the target buttock.

A subject will be considered a responder if these criteria are met in the randomized target buttock of that subject.

There will be 8 key secondary endpoints grouped as three families of 2 to 4 endpoints per family analyzed in hierarchical order.

Family #1—Four Endpoints:
  Proportion of 1-level PR-PCSS responders defined as subjects with ≥1-level improvement in PR-PCSS severity rating of the target buttock at Day 71 compared to Day 1
  Proportion of 2-level PR-PCSS responders defined as subjects with ≥2-level improvement in PR-PCSS severity rating of target buttock at Day 71 compared to Day 1
  Proportion of 1-level composite responders of target buttock (defined as subjects with an improvement in severity from baseline of at least 1 level of severity in the CR-PCSS of the target buttock assessed live by the Investigator and an improvement of severity from baseline of at least 1 level of severity in the PR-PCSS of the target buttock) at Day 71 compared to Day 1
  Proportion of 2-level composite responders of the non-target buttock at Day 71 compared to Day 1

Family #2—Two Endpoints:
  Proportion of 1-level SSRS responders defined as subjects who were at least slightly satisfied at Day 71 (SSRS rating ≥4)
  Change from baseline (Day 1) of the PR-CIS total score at Day 71

Family #3—Two Endpoints:
  Proportion of 1-level S-GAIS responders defined as subjects with ≥1-level improvement (improved, much improved or very much improved) in the S-GAIS assessment of the target buttock at Day 71
  Proportion of 2-level S-GAIS responders defined as subjects with ≥2-level improvement (much improved or very much improved) in the S-GAIS assessment of the target buttock at Day 71.

Example 5—Durability Evaluation

Durability was evaluated in follow-up to the Phase 2b study described above. Durability is defined as 1) the visit date that a subject became a 2-level composite responder until the first date of 2 sequential visits at which the assessment ratings return and are sustained to baseline ratings; and 2) the visit date that a subject became a 1-level composite responder until the first date of 2 sequential visits at which the assessment ratings return and are sustained at baseline ratings.

The evaluation was designed with an observational phase followed by a treatment phase (to treat untreated treatment areas or unsuccessful treated treatment areas) and associated observation phases. Blinded assessments (CR-PCSS and PR-PCSS) were collected on 237 subjects that were assessed at 6 months and 72 subjects that were assessed at 9 months. Of these subjects, 55 were treated with EN3835 and showed at least a 1-level improvement in the control study. Of these 55 composite responders, 54 had assessments conducted during the observation phase. The disposition of enrolled 1-level and 2-level composite responders is shown in Table 27. Of the 20 active-treated 2-level composite responders observed in study EN3835-201, 19 subjects enrolled in study EN3835-202.

TABLE 27

Subject Disposition-Observation Phase

| 1-Level Active Composite Responders with 1-Year Long-term Follow-up[a] | |
|---|---|
| Enrolled | 55 |
| Completed | 47 (85.5%) |
| Discontinued | 8 (14.5%) |
| Lost to Follow-up | 7 (12.7%) |
| Withdrawal by Subject | 1 (1.8%) |
| 2-Level Active Composite Responders with 1-Year Long-term Follow-up[b] | |
| Enrolled | 19 (34.5%) |
| Completed | 16 (29.1%) |
| Discontinued | 3 (5.5%) |

[a]1-Level Active Composite Responders: Subjects treated with EN3835 in Study EN3835-201 with at least 1 level of improvement on both CR-PCSS and PR-PCSS.
[b]2-Level Active Composite Responders: Subjects treated with EN3835 in Study EN3835-201 with at least 2 levels of improvement on both CR-PCSS and PR-PCSS.
Note:
Percentages are based on the number of "enrolled."

The durability in these composite responders at 6 months and 12 months in the unblinded portion of the OL observation phase of EN3835-202 and at 6 months and 9 months in the blinded assessment phase is summarized by level of composite responders.

Durability of 2-Level Composite Responders

Durability of drug effect at 6-months (Day 180) and 12-months (Day 360) was evaluated in study EN3835-202) in 19 and 16 two-level composite responders, ie, subjects that had an improvement of at least 2 levels of cellulite severity in both the PR-PCSS and CR-PCSS at Day 71, respectively. Of the 2-level composite responders, i.e., subjects that had an improvement of at least 2 levels of cellulite severity in both the PR-PCSS and the CR-PCSS, 100% (n=19) and 100% (n=16) demonstrated durability of effect at 6 months and 12 months, respectively (ie, no subject had returned to baseline for 2 consecutive visits; see Table 28).

TABLE 28

Number and Rate of 2-Level Active Composite Responders[a]-Open-label Phase

| | Duration-180 Days (N = 19) | | Duration-360 Days (N = 16) | |
|---|---|---|---|---|
| | Failures[b] | Rate | Failures[b] | Rate |
| 2-Level Composite Responders | 0 | 0% | 0 | 0% |

[a]2-Level Active Composite Responders: Subjects treated with EN3835 in Study EN3835-201 with at least 2 levels of improvement on both CR-PCSS and PR-PCSS.
[b]Failures are the Composite Responders whose CR-PCSS and PR-PCSS ratings returned to their Baseline or worse.
Note:
Percentages are based on "N" in each column.

In further support of the durability of effect in 2-level composite responders, the evaluations of cellulite severity in the initial phase of study EN3835-202 were performed by investigators and subjects while they were still blinded to the treatment that the subject had received in the DBPC study (EN3835-201). In this blinded phase of EN3835-202, 100% of 2-level composite responders showed durable effect of EN3835 at 6 months (n=18) and 9 months (Day 270; n=6), respectively (Table 29).

TABLE 29

Number and Rate of 2-Level Active Composite Responders[a]-Blinded Phase

| | Duration-180 Days (N = 18) | | Duration-270 Days (N = 6) | |
|---|---|---|---|---|
| | Failures[b] | Rate | Failures[b] | Rate |
| 2-Level Composite Responders | 0 | 0% | 0 | 0% |

[a]2-Level Active Composite Responders: Subjects treated with EN3835 in Study EN3835-201 with at least 2 levels of improvement on both CR-PCSS and PR-PCSS.
[b]Failures are the Composite Responders whose CR-PCSS and PR-PCSS ratings returned to their Baseline or worse.
Note:
Percentages are based on "N" in each column.

Durability of 1-Level Composite Responders

Durability of drug effect at 6 months (Day 180) and 12 months (Day 360) was evaluated in a currently ongoing OL extension study (study EN3835-202) in 54 and 47 one-level composite responders, ie, subjects that had an improvement of at least 1 level of cellulite severity in both the PR-PCSS and CR-PCSS at Day 71, respectively. Of these composite responders, 92.6% (ie, 100%–failure rate=% durable composite responders) and 97.9% demonstrated durability at 6 months and 12 months (ie, only 4 (7.4%) and 1 (2.1%) subjects had returned to baseline for 2 consecutive visits), respectively (Table 30).

TABLE 30

Number and Rate of 1-Level Active Composite Responders[a]-Open-label Phase

| | Duration-180 Days (N = 54) | | Duration-360 Days (N = 47) | |
|---|---|---|---|---|
| | Failures[b] | Rate | Failures[b] | Rate |
| 1-Level Composite Responders | 4 | 7.4% | 1 | 2.1% |

[a]1-Level Active Composite Responders: Subjects treated with EN3835 in Study EN3835-201 with at least 1 level of improvement on both CR-PCSS and PR-PCSS.
[b]Failures are the Composite Responders whose CR-PCSS and PR-PCSS ratings returned to their Baseline or worse.
Note:
Percentages are based on "N" in each column.

In further support of the durability of effect in 1-level composite responders, the evaluations of cellulite severity in the initial phase of study EN3835-202 were performed by investigators and subjects while they were still blinded to the treatment that the subject had received in the DBPC study (EN3835-201). In this blinded phase of EN3835-202, 92.2% and 100% of 1-level composite responders showed durable effect of EN3835 at 6 months and 9 months (Day 270) in 51 and 16 evaluable composite responders, respectively (Table 31). The treatment blind was broken at a time point that allowed Day 270 to be the longest interval evaluated in a blinded fashion.

TABLE 31

Number and Rate of 1-Level Active
Composite Responders$_a$-Blinded Phase

| | Duration-180 Days (N = 51) | | Duration-270 Days (N = 16) | |
|---|---|---|---|---|
| | Failures$^b$ | Rate | Failures$^b$ | Rate |
| 1-Level Composite Responders | 4 | 7.8% | 0 | 0% |

$^a$1-Level Active Composite Responders: Subjects treated with EN3835 in Study EN3835-201 with at least 1 level of improvement on both CR-PCSS and PR-PCSS.
$^b$Failures are the Composite Responders whose CR-PCSS and PR-PCSS ratings returned to their Baseline or worse.
Note:
Percentages are based on "N" in each column.

In summary of durability evaluations, the durability of effect at 6 months was shown in ≥92% of either 1-level or 2-level composite responders at 6 months in OL or double-blind (DB) phases of study EN3835-202. The durability at 12 months was shown in >97% of either 1-level or 2-level composite responders in the OL phase of EN3835-202; this durability was further supported by DB assessments at 9 months (Day 270) which showed 100% of composite responders evaluated at this time point had persistent drug effect. The results to date support the durability of EN3835 effect on cellulite for up to a year.

The embodiments of the invention described above are intended to be merely exemplary; numerous variations and modifications will be apparent to those skilled in the art. All such variations and modifications are intended to be within the scope of the present invention as defined in any appended claims.

What is claimed:

1. A method for rating the severity of, and treating, cellulite in an affected area of a human subject, the method comprising:
   rating the severity of the subject's cellulite using a validated photonumeric scale comprising 3 to 10 images showing an affected area of one or more example patients, the affected area in each of the 3 to 10 images of the example patients corresponding to the location of the affected area of the human subject, wherein each of the 3 to 10 images has a different severity rating comprising a numerical value, description, or both, the severity rating being based on a combination of two or more characteristics of cellulite selected from the group consisting of the number, depth, size, width, diameter, and distribution of dimples, wherein the photonumeric scale was validated using a test-retest reliability analysis; and
   injecting into the affected area a pharmaceutical formulation comprising a mixture of collagenase I and collagenase II obtained or derived from *Clostridium histolyticum* to thereby treat the cellulite.

2. The method of claim 1, wherein the affected area is the thigh or the buttock.

3. The method of claim 1, wherein the photonumeric scale produces a consistency among evaluators of at least 50%.

4. The method of claim 1, wherein the scale is a CR-PCSS scale that, when employed by a plurality of clinicians, at least 40% of the clinicians give the patient's area of cellulite the same cellulite severity rating from when the patients were screened and Day 1 pre-treatment.

5. The method of claim 4, wherein the clinicians provide the same rating in about 50%, or about 60%, or about 70%, or about 80%, or about 90%, or about 100% of patients.

6. The method of claim 1, wherein the scale is a CR-PCSS and a PR-PCSS that are employed to assess cellulite severity by an evaluation method selected from live assessment, by viewing digital images of the cellulite area, by viewing photographs of the cellulite area, and by viewing mirrored images of the cellulite area.

7. The method of claim 1, wherein the scale comprises a CR-PCSS scale.

8. The method of claim 1, wherein the scale comprises a PR-PCSS scale.

9. The method of claim 1, wherein the scale comprises both a CR-PCSS scale and a PR-PCSS scale.

10. The method of claim 1, wherein the photonumeric scale comprises an image showing an affected area having no evident cellulite and an image showing an affected area having severe cellulite.

11. The method of claim 10, wherein the image showing an affected area having no evident cellulite has a numerical value that is lower than the image showing an affected area having severe cellulite.

12. The method of claim 11, wherein the image showing an affected area having no evident cellulite:
   has a numerical value of 0; and/or
   contains no dimples, no depressions, no raised areas, or any combination thereof.

13. The method of claim 12, wherein the image showing an affected area having severe cellulite:
   has a numerical value of 4; and/or
   contains numerous deep dimples or ridges that cover most of the affected area, numerous undulations with alternating areas of protuberances and depressions of severe depth, or both.

14. A method for treating and improving evaluator consistency in rating the severity of cellulite in a buttock or a thigh of a human subject, the method comprising:
   providing a validated photonumeric scale comprising 3 to 10 images showing an affected area of one or more example patients, the affected area in each of the 3 to 10 images of the example patients corresponding to the location of the affected area of the human subject, wherein each of the 3 to 10 images has a different severity rating comprising a numerical value, description, or both, the severity rating being based on a combination of two or more characteristics of cellulite selected from the group consisting of the number, depth, size, width, diameter, and distribution of dimples, wherein the photonumeric scale was validated using a test-retest reliability analysis;
   comparing the scale to a corresponding characteristic of cellulite from a subject to obtain a rating of the level of severity of the cellulite of the subject; and
   injecting into the affected area a pharmaceutical formulation comprising a mixture of collagenase I and collagenase II obtained or derived from *Clostridium histolyticum* to thereby treat the cellulite.

15. The method of claim 14, wherein the scale comprises a CR-PCSS scale.

16. The method of claim 14, wherein the scale comprises a PR-PCSS scale.

17. The method of claim 14, wherein the scale comprises both a CR-PCSS scale and a PR-PCSS scale.

18. The method of claim 14, wherein the consistency among a plurality of evaluators is at least 50%.

19. The method of claim 14, wherein the consistency among a plurality of evaluators is about 50%, or about 60%, or about 70%, or about 80%, or about 90%, or about 100%.

* * * * *